US009789298B2

(12) United States Patent
Dehnad et al.

(10) Patent No.: US 9,789,298 B2
(45) Date of Patent: Oct. 17, 2017

(54) BONE IMPLANT AND SYSTEMS THAT CONTROLLABLY RELEASES SILVER

(71) Applicant: Silver Bullet Therapeutics, Inc., San Jose, CA (US)

(72) Inventors: Houdin Dehnad, El Granada, CA (US); Bohdan Wolodymyr Chopko, Mansfield, OH (US); Paul E. Chirico, Campbell, CA (US); Robert Vincent McCormick, Saratoga, CA (US)

(73) Assignee: Silver Bullet Therapeutics, Inc., San Jose, CA (US)

( * ) Notice: Subject to any disclaimer, the term of this patent is extended or adjusted under 35 U.S.C. 154(b) by 509 days.

(21) Appl. No.: 14/300,696

(22) Filed: Jun. 10, 2014

(65) Prior Publication Data

US 2014/0288607 A1 Sep. 25, 2014

Related U.S. Application Data

(63) Continuation of application No. 13/231,219, filed on Sep. 13, 2011, now Pat. No. 8,771,323.
(Continued)

(51) Int. Cl.
*A61B 17/86* (2006.01)
*A61B 17/56* (2006.01)
(Continued)

(52) U.S. Cl.
CPC ......... *A61M 37/00* (2013.01); *A61B 17/7266* (2013.01); *A61B 17/863* (2013.01);
(Continued)

(58) Field of Classification Search
CPC ............ A61B 17/7266; A61B 17/8625; A61B 17/863; A61B 17/864; A61B 17/8685; A61N 1/326
See application file for complete search history.

(56) References Cited

U.S. PATENT DOCUMENTS 2,998,007 A 8/1961 Herzog
3,921,632 A 11/1975 Bardani
(Continued)

FOREIGN PATENT DOCUMENTS

WO  WO 99/44538 A1  9/1999
WO  WO 00/47273 A1  8/2000
(Continued)

OTHER PUBLICATIONS

Dehnad et al.; U.S. Appl. No. 13/748,546 entitled "Bone Implant and Systems That Controllably Releases Silver," filed Jan. 23, 2013.
(Continued)

*Primary Examiner* — Nicholas Woodall
(74) *Attorney, Agent, or Firm* — Shay Glenn LLP

(57) ABSTRACT

Silver and/or zinc ion releasing implants, systems and method of operating, inserting and activating/inactivating them are described. In some variations the implant is configured as a bone implant that includes a bone-screw or intramedullary rod like body configured to receive a treatment cartridge having a plurality of ion-releasing members configured as an anode that can controllably engage with a catheter to turn galvanic release of ions on/off as desired. These devices may be configured to release silver ions (and/or zinc ions) above a predetermined level for a predetermined period of time and may maintain a concentration of ions over a relatively large volume of tissue. The ion-releasing members may be configured to reduce or prevent implant movement.

18 Claims, 9 Drawing Sheets

Related U.S. Application Data

(60) Provisional application No. 61/413,230, filed on Nov. 12, 2010, provisional application No. 61/438,162, filed on Jan. 31, 2011, provisional application No. 61/447,393, filed on Feb. 28, 2011, provisional application No. 61/465,350, filed on Mar. 18, 2011, provisional application No. 61/516,388, filed on Apr. 4, 2011.

(51) Int. Cl.

| | | |
|---|---|---|
| *A61M 37/00* | (2006.01) | |
| *A61F 2/28* | (2006.01) | |
| *A61K 33/38* | (2006.01) | |
| *A61K 33/30* | (2006.01) | |
| *A61B 17/72* | (2006.01) | |
| *A61C 19/06* | (2006.01) | |
| *A61N 1/30* | (2006.01) | |
| *A61B 17/68* | (2006.01) | |
| *A61B 17/80* | (2006.01) | |
| *A61B 17/00* | (2006.01) | |
| *A61C 8/00* | (2006.01) | |

(52) U.S. Cl.
CPC ........ *A61B 17/864* (2013.01); *A61B 17/8625* (2013.01); *A61B 17/8685* (2013.01); *A61C 8/0018* (2013.01); *A61C 19/06* (2013.01); *A61F 2/28* (2013.01); *A61K 33/30* (2013.01); *A61K 33/38* (2013.01); *A61N 1/306* (2013.01); *A61B 17/686* (2013.01); *A61B 17/80* (2013.01); *A61B 17/869* (2013.01); *A61B 2017/00889* (2013.01); *A61B 2017/561* (2013.01); *A61C 8/0012* (2013.01)

(56) References Cited

U.S. PATENT DOCUMENTS

| | | |
|---|---|---|
| 4,292,968 A | 10/1981 | Ellis |
| 4,314,554 A | 2/1982 | Greatbatch |
| 4,405,311 A | 9/1983 | Greatbatch |
| 4,615,705 A | 10/1986 | Scales et al. |
| 4,772,266 A | 9/1988 | Groshong |
| 4,849,223 A | 7/1989 | Pratt et al. |
| 5,290,271 A | 3/1994 | Jernberg |
| 5,372,599 A | 12/1994 | Martins |
| 5,383,935 A * | 1/1995 | Shirkhanzadeh ........ A61C 8/00 433/173 |
| 5,423,859 A | 6/1995 | Koyfman et al. |
| 5,454,886 A | 10/1995 | Burrell et al. |
| 5,505,735 A | 4/1996 | Li |
| 5,510,109 A | 4/1996 | Tomioka et al. |
| 5,549,603 A | 8/1996 | Feiring |
| 5,681,575 A | 10/1997 | Burrell et al. |
| 5,695,857 A | 12/1997 | Burrell et al. |
| 5,714,047 A | 2/1998 | Pedrazzini |
| 5,725,377 A | 3/1998 | Lemler et al. |
| 5,770,255 A | 6/1998 | Burrell et al. |
| 5,788,687 A | 8/1998 | Batich et al. |
| 5,958,440 A | 9/1999 | Burrell et al. |
| 5,985,308 A | 11/1999 | Burrell et al. |
| 6,117,296 A | 9/2000 | Thomson |
| 6,287,484 B1 | 9/2001 | Hausslein et al. |
| 6,312,469 B1 | 11/2001 | Gielen et al. |
| 6,425,887 B1 | 7/2002 | McGuckin et al. |
| 6,447,513 B1 | 9/2002 | Griggs |
| 6,451,003 B1 | 9/2002 | Prosl et al. |
| 6,458,092 B1 | 10/2002 | Gambale et al. |
| 6,458,889 B1 | 10/2002 | Trollsas et al. |
| 6,478,790 B2 | 11/2002 | Bardani |
| 6,500,165 B1 | 12/2002 | Frank |
| 6,522,918 B1 | 2/2003 | Crisp et al. |
| 6,558,388 B1 | 5/2003 | Bartsch et al. |
| 6,613,807 B2 | 9/2003 | Uhrich |
| 6,616,678 B2 | 9/2003 | Nishtala et al. |
| 6,716,895 B1 | 4/2004 | Terry |
| 6,719,987 B2 | 4/2004 | Burrell et al. |
| 6,773,429 B2 | 8/2004 | Sheppard, Jr. et al. |
| 6,830,747 B2 | 12/2004 | Lang et al. |
| 6,840,919 B1 | 1/2005 | Håkansson |
| 6,913,763 B2 | 7/2005 | Lerner |
| 6,936,006 B2 | 8/2005 | Sabra |
| 6,936,270 B2 | 8/2005 | Watson et al. |
| 6,960,215 B2 | 11/2005 | Olson, Jr. et al. |
| 7,147,865 B2 | 12/2006 | Fishman et al. |
| 7,179,849 B2 | 2/2007 | Terry |
| 7,223,227 B2 | 5/2007 | Pflueger |
| 7,255,713 B2 | 8/2007 | Malek |
| 7,456,012 B2 | 11/2008 | Ryttén et al. |
| 7,457,667 B2 | 11/2008 | Skiba |
| 7,632,277 B2 | 12/2009 | Woll et al. |
| 7,662,176 B2 | 2/2010 | Skiba et al. |
| 7,672,719 B2 | 3/2010 | Skiba et al. |
| 7,704,520 B1 | 4/2010 | Calhoun |
| 7,727,221 B2 | 6/2010 | Penner et al. |
| 7,824,699 B2 | 11/2010 | Ralph et al. |
| 7,846,162 B2 | 12/2010 | Nelson |
| 7,904,147 B2 | 3/2011 | Schneider et al. |
| 7,919,111 B2 | 4/2011 | Chudzik et al. |
| 7,951,853 B2 | 5/2011 | Ismail et al. |
| 7,955,636 B2 | 6/2011 | Terry |
| 7,985,415 B2 | 7/2011 | Giroux |
| 8,048,150 B2 | 11/2011 | Weber et al. |
| 8,052,743 B2 | 11/2011 | Weber et al. |
| 8,080,055 B2 | 12/2011 | Atanasoska et al. |
| 8,114,148 B2 | 2/2012 | Atanasoska et al. |
| 8,118,857 B2 | 2/2012 | VanCamp et al. |
| 8,178,120 B2 | 5/2012 | Vandesteeg et al. |
| 8,221,396 B2 | 7/2012 | Dehnad et al. |
| 8,236,046 B2 | 8/2012 | Weber |
| 8,267,992 B2 | 9/2012 | Atanasoska et al. |
| 8,292,932 B2 | 10/2012 | Matthis et al. |
| 8,309,216 B2 | 11/2012 | Ohrlander et al. |
| 8,591,531 B2 | 11/2013 | Buevich et al. |
| 8,636,753 B2 | 1/2014 | Buevich et al. |
| 8,771,323 B2 | 7/2014 | Dehnad et al. |
| 8,999,367 B1 | 4/2015 | Dehnad et al. |
| 9,114,197 B1 | 8/2015 | Dehnad et al. |
| 9,452,242 B2 | 9/2016 | Dehnad et al. |
| 2002/0029043 A1* | 3/2002 | Ahrens ............... A61B 17/866 606/309 |
| 2002/0031601 A1 | 3/2002 | Darouiche et al. |
| 2002/0082679 A1 | 6/2002 | Sirhan et al. |
| 2002/0111603 A1 | 8/2002 | Cheikh |
| 2002/0143302 A1 | 10/2002 | Hinchliffe et al. |
| 2003/0050689 A1 | 3/2003 | Matson |
| 2003/0065292 A1 | 4/2003 | Darouiche et al. |
| 2004/0039441 A1 | 2/2004 | Rowland et al. |
| 2004/0223944 A1 | 11/2004 | Capelli |
| 2004/0267234 A1 | 12/2004 | Heart et al. |
| 2005/0004558 A1 | 1/2005 | Gambale et al. |
| 2005/0125054 A1 | 6/2005 | Bhat et al. |
| 2005/0152949 A1 | 7/2005 | Hotchkiss et al. |
| 2005/0177103 A1 | 8/2005 | Hunter et al. |
| 2005/0181004 A1 | 8/2005 | Hunter et al. |
| 2005/0256525 A1 | 11/2005 | Culbert et al. |
| 2005/0271701 A1 | 12/2005 | Cottone et al. |
| 2006/0004431 A1* | 1/2006 | Fuller ................... A61B 17/86 607/116 |
| 2006/0030872 A1 | 2/2006 | Culbert et al. |
| 2006/0041182 A1 | 2/2006 | Forbes et al. |
| 2006/0264698 A1 | 11/2006 | Kondonis et al. |
| 2007/0016163 A1 | 1/2007 | Santini, Jr. et al. |
| 2007/0141106 A1 | 6/2007 | Bonutti et al. |
| 2007/0168012 A1 | 7/2007 | Ragheb et al. |
| 2007/0179609 A1 | 8/2007 | Goble et al. |
| 2007/0244548 A1 | 10/2007 | Myers et al. |
| 2007/0260054 A1 | 11/2007 | Chudzik |
| 2007/0298377 A1 | 12/2007 | Kenealy et al. |
| 2008/0009888 A1 | 1/2008 | Ewers et al. |
| 2008/0058733 A1 | 3/2008 | Vogt et al. |
| 2008/0109034 A1 | 5/2008 | Mather et al. |
| 2008/0147186 A1 | 6/2008 | Joshi et al. |

(56) References Cited

U.S. PATENT DOCUMENTS

| | | |
|---|---|---|
| 2008/0195033 A1 | 8/2008 | Eagleson et al. |
| 2008/0195223 A1 | 8/2008 | Eddin et al. |
| 2008/0255618 A1 | 10/2008 | Fisher et al. |
| 2008/0319424 A1 | 12/2008 | Muni et al. |
| 2009/0004239 A1 | 1/2009 | Ladet et al. |
| 2009/0005867 A1 | 1/2009 | Lefranc et al. |
| 2009/0005869 A1 | 1/2009 | Laurencin et al. |
| 2009/0012350 A1 | 1/2009 | Tihon |
| 2009/0035342 A1 | 2/2009 | Karandikar et al. |
| 2009/0036744 A1 | 2/2009 | Vayser |
| 2009/0099613 A1 | 4/2009 | Vilims |
| 2009/0112236 A1 | 4/2009 | Stopek |
| 2009/0204129 A1 | 8/2009 | Fronio |
| 2009/0248048 A1 | 10/2009 | Milbocker |
| 2010/0076463 A1 | 3/2010 | Mavani et al. |
| 2010/0092531 A1 | 4/2010 | Odermatt et al. |
| 2010/0131051 A1 | 5/2010 | Peterson |
| 2010/0217370 A1 | 8/2010 | Scheuermann et al. |
| 2010/0249783 A1 | 9/2010 | Triue |
| 2010/0292756 A1* | 11/2010 | Schneider ............... A61N 1/326 607/50 |
| 2010/0326835 A1 | 12/2010 | Speitling |
| 2010/0331966 A1 | 12/2010 | Borck |
| 2011/0091515 A1 | 4/2011 | Zilberman et al. |
| 2011/0125287 A1 | 5/2011 | Hotter et al. |
| 2011/0130774 A1 | 6/2011 | Criscuolo et al. |
| 2011/0153027 A1 | 6/2011 | Behan |
| 2011/0200655 A1 | 8/2011 | Black et al. |
| 2011/0257666 A1 | 10/2011 | Ladet et al. |
| 2012/0148633 A1 | 6/2012 | Sun et al. |
| 2012/0251592 A1 | 10/2012 | Neff et al. |
| 2012/0323220 A1 | 12/2012 | Mackay et al. |
| 2013/0005829 A1 | 1/2013 | Jamiolkowski et al. |
| 2013/0018448 A1 | 1/2013 | Folan et al. |
| 2013/0045266 A1 | 2/2013 | Choi et al. |
| 2013/0158571 A1 | 6/2013 | Meneghin et al. |
| 2013/0172915 A1 | 7/2013 | Thomas et al. |
| 2013/0224276 A1 | 8/2013 | Hunter et al. |
| 2013/0245783 A1 | 9/2013 | Thull |
| 2013/0295184 A1 | 11/2013 | Choi et al. |
| 2015/0359946 A1 | 12/2015 | Dehnad et al. |
| 2016/0157907 A1 | 6/2016 | Dehnad et al. |
| 2017/0014607 A9 | 1/2017 | Dehnad et al. |

FOREIGN PATENT DOCUMENTS

| | | |
|---|---|---|
| WO | WO 02/09767 A2 | 2/2002 |
| WO | WO 03/049798 A2 | 6/2003 |
| WO | WO 2004/006885 A2 | 1/2004 |
| WO | WO 2004/026357 A1 | 4/2004 |
| WO | WO 2004/045549 A2 | 6/2004 |
| WO | WO2004/059027 A2 | 7/2004 |
| WO | WO 2005/049105 A2 | 6/2005 |
| WO | WO2005/051448 A1 | 6/2005 |
| WO | WO 2006/135479 A2 | 12/2006 |
| WO | WO 2007/076376 A2 | 7/2007 |
| WO | WO2007/097790 A1 | 8/2007 |
| WO | WO 2007/109069 A2 | 9/2007 |
| WO | WO 2007/117214 A1 | 10/2007 |
| WO | WO 2011/031789 A1 | 3/2011 |
| WO | WO 2011/127149 A1 | 10/2011 |
| WO | WO 2013/004727 A1 | 1/2013 |

OTHER PUBLICATIONS

Dehnad et al.; U.S. Appl. No. 13/527,389 entitled "Bone implants for the treatment of infection," filed Jun. 19, 2012.

Dehnad et al.; U.S. Appl. No. 14/302,352 entitled "Bioabsorbable substrates and systems that controllably release antimicrobial metal ions," filed Jun. 11, 2014.

* cited by examiner

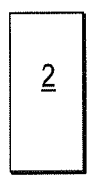
FIG. 1A
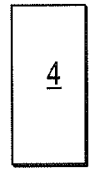
FIG. 1B
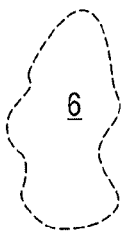
FIG. 1C
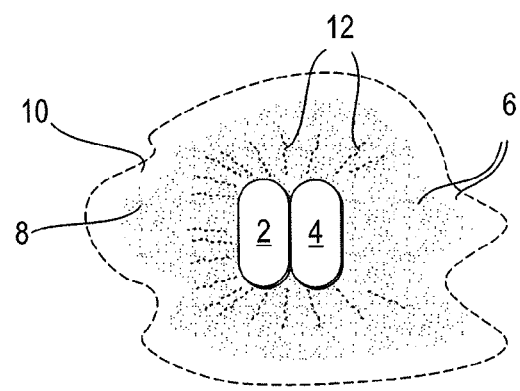
FIG. 1D
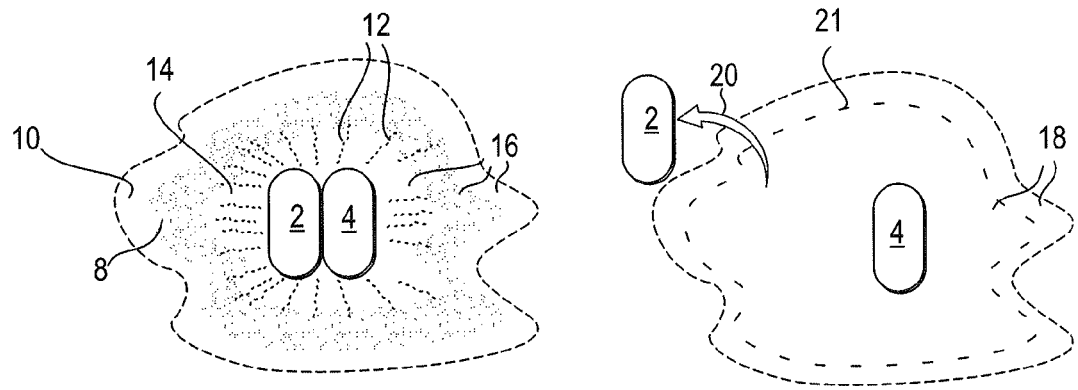
FIG. 1E
FIG. 1F

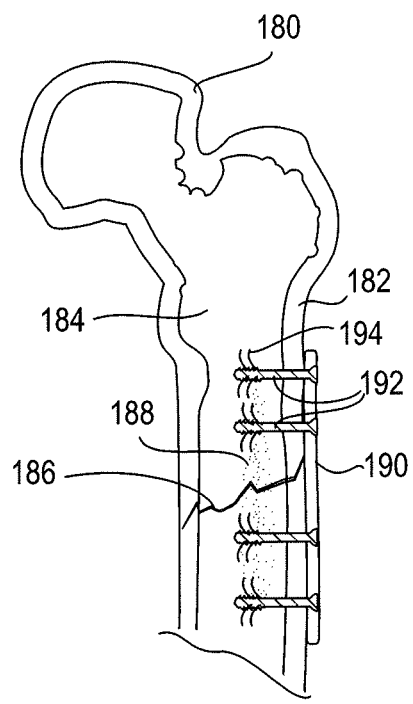 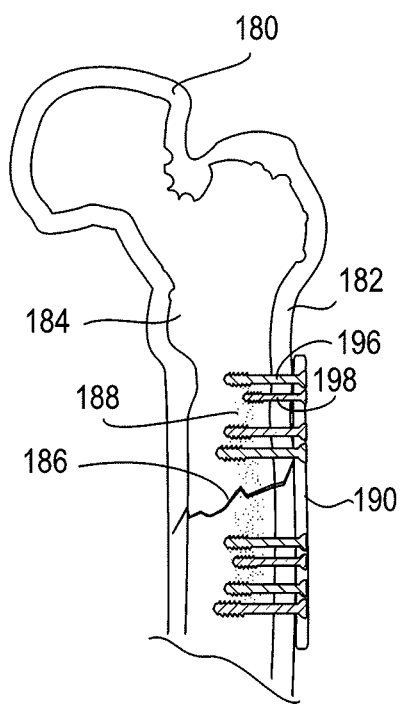
FIG. 13A  FIG. 13B
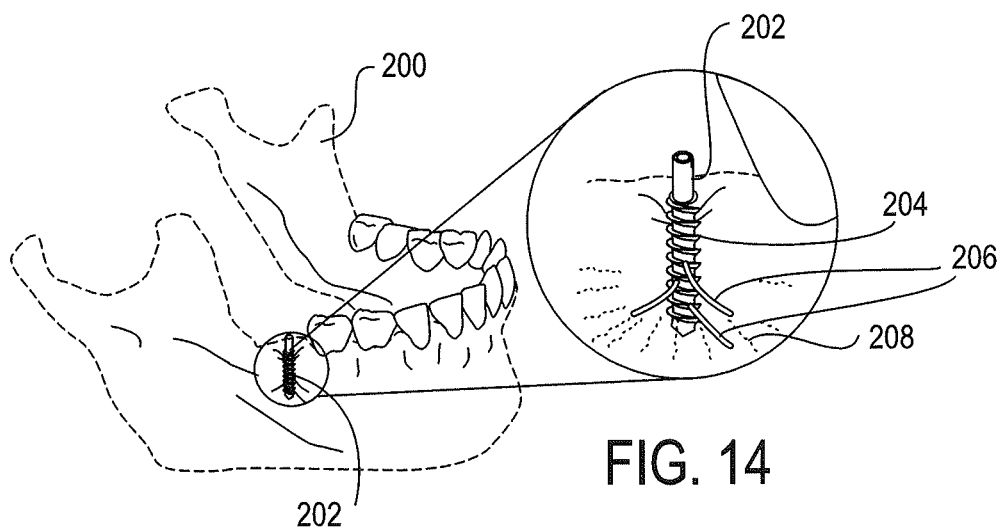
FIG. 14

BONE IMPLANT AND SYSTEMS THAT CONTROLLABLY RELEASES SILVER

CROSS REFERENCE TO RELATED APPLICATIONS

This patent application is a continuation of U.S. patent application Ser. No. 13/231,219, filed on Sep. 13, 2011, and titled "BONE IMPLANT AND SYSTEMS THAT CONTROLLABLY RELEASES SILVER," Publication No. US-2012-0123485-A1, which claims priority to the following U.S. provisional patent applications: U.S. Provisional Patent Application No. 61/413,230, filed on Nov. 12, 2010, and titled "SILVER ELUTING BONE IMPLANTS AND METHODS OF USE;" U.S. Provisional Patent Application No. 61/438,162, filed on Jan. 31, 2011, and titled "BONE SUPPORTING IMPLANTS WITH ANTIBACTERIAL PROPERTIES;" U.S. Provisional Patent Application No. 61/447,393, filed on Feb. 28, 2011, and titled "INTRAMEDULLARY (INTRAOSSEAL) ROD, NAIL OR CATHETER WITH GALVANICALLY PRODUCED ANTIBACTERIAL PROPERTIES;" U.S. Provisional Patent Application No. 61/465,350, filed on Mar. 18, 2011, and titled "ANTIMICROBIAL IMPLANT TO PROVIDE MECHANICAL SUPPORT FOR A BORE THAT UTILIZES A GALVANIC POTENTIAL BETWEEN TWO OR MORE METALS TO CREATE IONS THAT ARE GERMICIDAL AND/OR ANTIFUNGAL;" U.S. Provisional Patent Application No. 61/516,388, filed on Apr. 4, 2011, and titled "GALVANIC ANTIMICROBIAL BONE SCREW FOR THE TREATMENT OF DISEASED, FRACTURE OR MISALIGNED BONE AND TO PROMOTE BONE GROWTH AND REGENERATION."

INCORPORATION BY REFERENCE

All publications and patent applications mentioned in this specification are herein incorporated by reference to the same extent as if each individual publication or patent application was specifically and individually indicated to be incorporated by reference.

BACKGROUND

Osteomyelitis is an infection of a bone by a microorganism such as bacteria or fungi. Diabetes, joint replacement, trauma, and injected drug use can lead to osteomyelitis. As people live longer, incidences of osteomyelitis are expected to increase. To complicate matters, an infection, such as following joint replacement surgery, can occur long after the incision has been closed. An infection buried in a bone can be difficult to detect; it is not visible to the eye and taking a culture sample is difficult and painful. Once diagnosed, antibiotics can eliminate many infections. Unfortunately, microorganisms are developing resistances rendering existing antibiotics useless. Reports of patients infected with microorganisms resistant to regular and "last resort" antibiotics are increasing in number. For these patients, there are few or no effective options. The problem is expected to become worse as microorganisms exchange genetic material and more species become resistant to antibiotics. Prophylactic use of antibiotics, although commonly done, is discouraged because it may increase antibiotic resistance. Infection with methicillin resistant Staphylococcus aureus (MRSA) is a significant health problem that is expected to worsen. Additionally, microorganisms on the surface of an artificial joint or other implanted device can cooperate to create an impervious layer, called a biofilm. A biofilm may form a mechanical barrier to an antibiotic.

Silver is known to be antimicrobial and has been used (primarily as a coating) in various medical devices with limited success. Both active (e.g., by application of electrical current) and passive (e.g., galvanic) release of silver ions have been proposed for use in the treatment and prevention of infection. However, the use of silver-releasing implants have been limited because of the difficulty in controlling and distributing the release of silver ions as well as the difficulty in maintaining a therapeutically relevant concentration of silver ions in an appropriate body region. Zinc shares many of the same antimicrobial properties of silver, but have been less commonly used, and thus even less is known about how to control the amount and distribution of the release of silver ions to treat and/or prevent infection.

Thus, it would be highly desirable to provide device systems and methods for the controlled release (particularly the controlled galvanic release) of a high level of silver, zinc or silver and zinc ions into the tissue for a sufficient period of time to treat or prevent infection.

Specifically, known systems and devices that have attempted to use ions (e.g., silver and/or zinc) to treat infection have suffered from problems such as: insufficient amounts of ions released (e.g., ion concentration was too low to be effective); insufficient time for treatment (e.g., the levels of ions in the body or body region were not sustained for a long enough period of time); and insufficient region or volume of tissue in which the ion concentration was elevated (e.g., the therapeutic region was too small or limited, such as just on the surface of a device). Further, the use of galvanic release has generally been avoided or limited because it may effectively corrode the metals involved, and such corrosion is generally considered an undesirable process, particularly in a medical device.

In general, controlled release of silver and/or zinc ions would be beneficial. Control of the release of ions may allow the treatment of the patient to be regulated by turning the release on/off. In general, silver coated devices do not typically allow for the controlled release of ions. Silver coatings or impregnations do not typically allow controlled release, because they are always "on" (e.g., always releasing silver) to some degree. Zinc coatings on traditional implants may suffer from the same problem. Since release depends on the ionic concentration of body fluids, the actual release (and therefore concentration) of ions may be difficult to predict and control.

Therapeutically, the level of silver and/or zinc ions released into a body is important, because it may determine how effective the antimicrobial ions are for treating or preventing infection. As described in greater detail below, the amount or ions released galvanically may depend on a number of factors which have not previously been well controlled. For example, galvanic release may be related to the ratio of the anode to the cathode (and thus, the driving force) as well as the level of oxygen available; given the galvanic reaction, the level of oxygen may be particularly important for at the cathode. Insufficient oxygen at the cathode may be rate-limiting for galvanic release.

For example, with respect to silver, it has been reported that a concentration of 1 mg/liter of silver ions can kill common bacteria in a solution. Silver ions may be generated a galvanic system with silver as the anode and platinum or other noble metal as the cathode. However one of the challenges in designing a galvanic system for creation of silver ion in the body that has not been adequately addressed is the appropriate ratios of the areas of the electrodes (e.g., anode to cathode areas) in order to create the germicidal level of free silver ions. One challenge in designing a galvanic system is addressing the parasitic loss of current due to formation of silver chloride via reaction:

$$AgCl + e \rightarrow Ag + Cl(-) \quad Eo=0.222 \text{ volts}$$

We herein propose that it may be beneficial to have an area of the cathode under common biological condition that is at least larger than 8% of the silver area to sustain the germicidal level of silver ions. For the purpose of this discussion, the following assumptions have been made: for a concentration of: $[H+]=10^{\wedge}(-7)$ moles/liter; $[OH-]=10^{\wedge}(-7)$ moles/liter; $[O2]=5*10^{\wedge}(-3)$ moles/liter in the capillary; $[Cl-]=0.1$ moles/liter. The values of the following were also assumed (as constants or reasonable approximations): Faraday's constant, F=96000 coulombs/mole; diffusivity of oxygen=0.000234 cm2/sec; diffusivity of Ag+= $10^{\wedge}(-6)$ cm2/sec; diffusivity of Cl-=$10^{\wedge}(-6)$ cm2/sec; R, Gas constant=8.314 J K$^{-1}$ mol$^{-1}$; T, temp. K; Mw of silver=108 grams/mol; germicidal concentration of silver=$10^{\wedge}(-5)$ mol/liter.

At equilibrium, for a galvanic cell it is acceptable to assume that the two electrodes are at the same potential. Using the Nernst equation, the equilibrium concentration of oxygen when the silver ion is at the germicidal level may be calculated:

$$E=Eo-(RT/nF)\ln[(\text{Activity of products})/(\text{activity of reactants})]$$

$$E=Eo-(0.0592/n)\text{Log}[(\text{product})/(\text{reactant})]$$

For the half cell reaction at the anode (silver electrode): Ag→Ag(+)+e(−). This reaction is written as a reduction reaction below:

$$Ag(+) + e(-) \rightarrow Ag \quad Eo=0.800 \text{ volt} \quad \text{eq. (1)}$$

$[Ag+]=1$ mg/liter*(gr/1000 mg)*(1 mol/108 (Mw of Ag))=$10^{\wedge}(-5)$ Ag+ mole/liter; E=0.800−(0.0592/1) log $[1/(10^{\wedge}(-5))]$. Based on this, the resulting E= 8.00−(0.0592*5)=0.504 volt.

For the cathode, the reactions are:

$$O_2 + 2H_2O + 4e(-) \rightarrow 4OH(-) \quad Eo=0.401 \text{ volt} \quad \text{eq. (2)}$$

$$O_2 + 4H(+) + 4e(-) \rightarrow 2H_2O \quad Eo=1.229 \text{ volt} \quad \text{eq. (3)}$$

In dilute aqueous solutions these two reactions are equivalent. At equilibrium the potential for the two half-cell potentials must be equal:

$$E=0.401-(0.0592/4)\log\{[OH(-)]^4/[O2]\}$$

$$E(\text{silver})=0.504=0.401-(0.0592/4)\log\{[10^{\wedge}-7]^4/[O2]\}$$

Solving for $[O_2]$, the result is: $[O_2]=10^{\wedge}(-21)$ atm. The result of this analysis is that, thermodynamically speaking, as long as the concentration of oxygen is above $10^{\wedge}(-21)$, the concentration of the sliver ion could remain at the presumed germicidal level.

However, a parasitic reaction to creation of silver ions is the formation of AgCl due to reaction of Cl− at the silver electrode. The half-cell potential for this reaction is:

$$AgCl + e(-) \rightarrow Ag + Cl(-) \quad Eo=0.222$$

Solving the Nernst equation for this reaction with E=0.504, the concentration of chloride $[Cl-]=2\times10^{\wedge}(-5)$. The importance of this reaction becomes apparent in evaluating the current needed to compensate for the losses of current due to this reaction and the increased in ratio of the area of the cathode to the anode.

The current density per untill area requirements of the device can be estimated by combining Fick's and Faraday equations: the silver losses due to diffusion of silver from the device can be calculated using the Fick's equation:

$$j=D[C(d)-C(c)]/d \quad \text{Fick's equation}$$

The current needed to create the silver ions (A/cm2): i=j*n*F, where, j is the mass flux, C(d) is the concentration of the silver at the device and C(c) is concentration of silver at the capillary bed (=0). D is the diffusion coefficient of silver ($10^{\wedge}(-6)$) cm2/sec, d is the average distance of the device from the capillary bed (assumed to be =0.5 cm in the bone), F is Faraday's constant (96000 col./mol), and n is the charge number.

The combination of the two equations for silver diffusion gives:

$$i(Ag)=D*\cdot n\cdot F(C(d))/d$$

Thus:

$$i(Ag) = \{10^{\wedge}(-6) * 1 * (10^{\wedge}(-5))(96000) * (5*10^{\wedge}(-3))/0.5\} *$$

$$(1 \text{ liter}/1000 \text{ cc})$$

$$= 2*10^{\wedge}(-9) \text{Amp/cm}^2$$

The current needed to create the silver ions at the desired concentration is approximately 2 nanoAmp/cm². Similarly, the current density (A/cm2) required to reduce the chloride ions from biological level (0.1 molar) to the desired level of $2*10^{\wedge}(-5)$ molar could be calculated. For this equation the approximate values of the constants are $D=10^{\wedge}(-6)$, d=0.1 cm. The change in the Chloride concentration it assumed to be $(0.1-2*10^{\wedge}(-5))=0.1$. The current needed to feed the parasitic reaction can then be determined:

$$i(cl) = \{10^{\wedge}(-6) * (1) * (96000) * (0.1)/(0.1)\} * (1 \text{ lit}/1000 \text{ cc})$$

$$= 9.6*10^{\wedge}(-5)$$

$$= 96 \text{ microAmp/Cm}^2$$

The total anodic current needed is: i(Ag)+i(Cl)= i(anodic)=96 microAmps/cm². On the cathode, the reaction limitation is the flux of oxygen form the source to the surface of the electrode. The max i(cathodic) current could be approximated to:

$$i(O2) = \{(0.000324)*(4)*(96000)*(5*10^{\wedge}(-3))/(0.5)\}(1 \text{ lit}/1000 \text{ cc})$$

$$1.24*10^{\wedge}(-3) \text{Amps/cm}^2$$

Since the total cathodic current must be equal to total Anodic current:

$$i(\text{cathodic}) * \text{Area of the cathode} =$$

$$i(\text{anodic}) * \text{Area of Anode} \Rightarrow \text{Area of the Cathode}/\text{Area}$$

$$\text{of the anode} = (96*10^{\wedge}(-6)/(1.24*10^{\wedge}(-3)) = 0.077$$

This suggests that the area of the cathode must be at least equal to 8% of that of anode.

In addition to the ratio of the cathode to the ratio of the anode, another factor affecting the release of silver ions that has not previously been accounted for in galvanic release of silver to treat infection is the concentration of oxygen needed.

The concentration of the oxygen needed to power the galvanic system is typically higher than that of the equilibrium concentration, since the system must overcome the activation energy of the reactions (over-potential) and supply the additional current. In the model below we evaluated the concentration of the oxygen needed to overcome the activation energy for the reactions. Using the Tafel equation:

$$\eta = \beta \log [i/io]$$

where i=current density, η=the over-potential, β=overpotential voltage constant, and io=intrinsic current density. For platinum, the oxygen over-potential constants are: $\beta=0.05$ volt and $io=10^{(-9)} A/m^2$. Using $i=9.6*10^{(-5)}$ Amp then:

$$\eta = 0.05 \log [9.6*10^{(-5)}/(10^{(-9)})]$$

$$\eta = 0.25 \text{ volt}$$

Adding the over potential to the potential at the equilibrium (0.501 volts), and the total working half-potential needed at the cathode becomes equal to (0.501+0.25)=0.751.

Using the Nernst equation to determine the concentration of oxygen at the cathode:

$$E = 0.751 = 0.401 - (0.0592/4) \log \{[OH(-)]^4/[O2]\}$$

Thus, the concentration of oxygen at the electrode should be at least $7*10^{(-5)}$ mole.

The results of this analysis show that an implanted galvanic system would benefit from having an area of the cathode to the area of the anode ($A_{cathode}/A_{anode}$) of greater that about 8% and the concentration of the oxygen at the site of implant to be at least $7*10^{(-5)}$ moles per liter, which may avoid rate-limiting effect.

Thus, to address the problems and deficiencies in the prior art mentioned above, described herein are systems, methods and devices for prophylactically treating a patient to prevent an infection and options for eliminating an existing infection, including those untreatable by any existing treatments. Described below are implants and methods for preventing and treating bone infections using an implantable, controllable, and rechargeable bone screws.

SUMMARY OF THE DISCLOSURE

The systems, devices and methods described herein may generally be used to treat or prevent infection, including bone infections such as osteomyelitis by the controlled release of silver, zinc, or silver and zinc ions. In particular, the systems, methods and devices described herein may be configured to allow controllable galvanic release of ions (e.g., silver, zinc or silver and zinc ions) to treat or prevent infection. Many of the variations described herein may be used in conjunction with one or more implants that also structurally or therapeutically support the patient, including particularly the patient's bones.

In general, any of the implants described herein may be used to treat bone and/or soft tissue. In some variations the implants are bone implants specifically, and may be configured to support as well as treat the bone. For example, the implant may be used to secure (as a screw, nail, bolt, clamp, etc.) another member such as a plate, rod, or the like, or the implant may itself include a support member such as a rod, plate, etc. In some variations, the implant is a soft tissue implant that is configured to be secured within non-bone body structures.

Although many of the examples described herein are illustrated describing the release of silver ions, any of the devices, methods and systems described may be configured for the release of zinc ions instead of, or in addition to, silver ions. It may be beneficial to release both zinc and silver ions. In some situations it may be beneficial to release zinc rather than silver, or vice versa. For example, variations of the devices releasing zinc may be used preferentially when the infection targeted is resistant to silver. Zinc may also "corrode" faster, e.g., releasing ions more quickly and/or at a higher concentration than silver, which may be avoided or exploited depending upon the context.

Described herein are systems, devices and methods for the controlled release of silver, zinc, or silver and zinc ions to treat or prevent infection that may address many of the problems identified above. For example, described herein are devices configured for the galvanic release of ions that may be controlled with an on/off switch mechanism. For example, in some variations the galvanic relationship can be regulated remotely (before or after the silver and/or zinc releasing implant has been inserted into the body). In some variations the systems and device may be configured so that the implant includes a separable or separate cathode and/or anode. The anode region (e.g., silver, zinc, or silver and zinc anode) may be placed central to the treatment region while the cathode could be positioned in an oxygen-rich region that may be separate from the treatment region (e.g., oxygenated blood). This may allow effective treatment of even relatively anoxic regions, including bone.

The devices and systems described herein may also be configured to regulate the effective cathode active surface area and anode active surface area (e.g., making the cathode surface area much larger than the effective anode surface area). For example, the cathode active surface area may be 5% greater (e.g., Au/Palladium), 8% (e.g., Au/Pt), 10% (e.g., Au/Ag), etc. than the anode surface area.

For example described herein are implants, including bone implants, for providing antimicrobial treatment to a region of a bone (and/or surrounding tissues) In some variations the implant includes: an elongate cannulated body having a threaded outer region; at least one exit channel extending from the cannulated body and out through the threaded outer region; and one or more silver, zinc, or silver and zinc release members configured to extend from the cannulated body and out of the exit channel.

The ion release members may be configured as part of a removable treatment cartridge that is configured to fit within the cannulated body of the implant so that the one or more ion release members extend from the cannulated body. Note, as used herein the phrase "treat" and "treatment" may include acute and prophylactic treatments.

In the simplest variation, the implant is configured as a bone screw that is hollow or contains a hollow inner body region into which a replaceable/rechargeable treatment cartridge may be inserted and/or removed. The cartridge may be itself screwed into the body, or it may be otherwise secured within the body. The cartridge may include one or more (e.g., a plurality) of ion release members extending or extendable from the cartridge and therefore the implant. An ion release member may be configured to release silver, zinc or silver and zinc. In general an ion release member may be configured as an elongate member such as an arm, wire, branch, or the like. The ion release member may be a wire (e.g., silver wire), or it may be a coated member such as a Nitinol or other shape-memory member, including a silver and/or zinc coating. As mentioned, the implant (or the treatment cartridge portion) may include a plurality of ion release members.

An implant may have one or more exit channels. In general the exit channels may be openings from the inner hollow region (e.g. cannulated body) of the implant through a side wall of the implant and out, possibly in the threaded region. Thus, in some variations the exit channel is configured to deflect the one or more ion release members away from a long axis of the implant. For example, the exit channel may be configured to deflect the one or more ion release members against a thread of the outer threaded region so that it deflects away from the implant. In some variations a plurality of exit channels extending through the cannulated body.

An implant may also include a guide (or guide element, including a rail, keying, etc.) within the channel configured to guide or direct the one or more ion release member out of the cannulated body from the at least one exit channel. The exit channels may be configured to allow tissue (e.g., bone) ingrowth, which may help with stability of the device once implanted. For example, the exit channels may be slightly oversized compared to the ion release members, permitting or encouraging in-growth. In some variations the exit channels may be doped or otherwise include a tissue-growth enhancing or encouraging factor (such as a growth factor), or may be otherwise modified to encourage tissue growth.

In some variations the treatment cartridge may include a silver, zinc or silver and zinc anode and the elongate body includes a cathode, wherein the cathode has a higher redox potential than the anode. The cathode may have an irregular surface, or a high-surface area (e.g., per unit volume); for example, the cathode may be formed of a foamed metal. In general the surface area of the cathode may be substantially greater than the surface are of the anode.

The treatment cartridge may be replaceable. For example, a treatment cartridge may be configured to be removable from the cannulated body of the implant in situ, without removing the body of the implant from the device. Thus, the body of the implant may be structurally supportive (e.g., supporting the bone) while the silver-releasing portion may be re-charged by inserting another (replacement) cartridge after the previous cartridge has corroded. For example, an elongate cannulated body may be configured as bone screw (e.g., an intramedullary bone screw).

In some variations, an implant for providing antimicrobial treatment to a tissue includes: an elongate body having a threaded outer screw region; an inner channel within the elongate body; a plurality of exit channels extending from the inner channel and out through the threaded outer screw region; and a treatment cartridge configured to fit within the inner channel, the cartridge comprising a plurality of ion release members configured to extend out of the exit channels.

As mentioned, the inner channel may include a guide element configured to direct the release members out of the exit channels. The guide element may be a shaped channel region (e.g., keying) or the like, configured to regulate the interaction between the implant body and the cartridge (see, e.g., guide element 99 in FIGS. 7B-7C).

Any of the variations described herein may also include a tissue sampling feature. For example, the treatment cartridge may comprise a sampler element configured to obtain a sample from a patient in whom a bone implant has been implanted. A sampler element may be a region configured to scrape, cut or otherwise remove a sample of tissue, particularly as the cartridge is removed from the implant. The sampled tissue may be examined for infection or the like.

Also described herein are systems for the controllable galvanic release of silver, zinc or silver and zinc ions from an implant to prevent or treat infection. For example, a system may include: a threaded implant configured to be inserted into a bone and to hold an ion releasing treatment cartridge; a cathode on the implant, the cathode comprising a material having a higher redox potential than the material of the anode (e.g., silver, zinc or silver and zinc); a treatment cartridge comprising a silver, zinc or silver and zinc anode, wherein, when the treatment cartridge is held by the implant, the cathode is in electrical contact with the anode, driving the galvanic release of ions from the release cartridge; and a switchable control configured to regulate electrical contact between the anode and cathode.

In any of the variations described herein, the cathode may comprise a material selected from the group consisting of: palladium, platinum, and gold. The cathode and anode may be configured to generate a galvanic current greater than about 0.2 µamps. The treatment cartridge may include a plurality of ion release members configured to extend from the implant when the cartridge is engaged therewith.

As mentioned above, any of the variations described herein may include a switchable control configured to turn on and/or off the galvanic activity between the anode and cathode. In some variations the switch may be configured to electrically separate the anode and cathode preventing or limiting the galvanic reaction. In some variations, the switchable control may be configured for remote activation. For example, a switchable control may include a magnet.

Also described herein are methods of controllably delivering silver ions from an implant to prevent or treat infection. Such a method may include the steps of: engaging an implant with a removable ion-releasing treatment cartridge, wherein the treatment cartridge comprises an anode (silver, zinc or silver and zinc), and wherein the implant includes a cathode comprising a material having a higher galvanic potential than the anode, further wherein the cathode has a greater active surface area than the active surface area of the anode; and activating a switchable control to initiate the galvanic release of ions from the treatment cartridge by placing the cathode in electrical contact with the anode.

The step of engaging the implant with the removably treatment cartridge may include coupling the treatment cartridge with an implant already inserted into a patient. The method may also include the step of placing at least a portion of the cathode in communication with a source of oxygen at a concentration of greater than $7 \times 10^{-5}$ mol/L. In some variations, the implant may be implanted into a bone.

Also described are systems for the release of ions from an implant to prevent or treat infection, the system including: an implant configured to hold a silver, zinc or silver and zinc release treatment cartridge; a removable treatment cartridge comprising a silver, zinc or silver and zinc anode; and a cathode comprising a material having a higher redox potential than the anode, wherein the cathode is configured to be positioned separately from the anode and in contact with an oxygen-rich environment when the implant is implanted; wherein, when the treatment cartridge is held by the implant, the cathode is in electrical contact with the anode, driving the galvanic release of ions from the treatment cartridge.

BRIEF DESCRIPTION OF THE DRAWINGS

FIGS. 1A-1F illustrate the general concept of galvanic release of silver ions.

FIGS. 13A and 13B illustrate two variations of silver eluting bone implants as described.

FIG. 14 illustrates another variation of an implant configured for use as a dental device. Similarly.

DETAILED DESCRIPTION

Figure 2A:
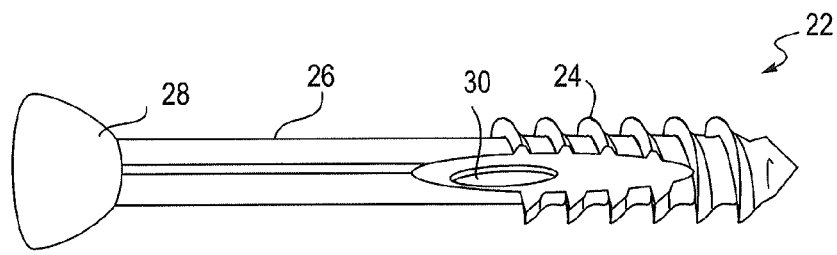
FIGS. 2A and 2B illustrate one variation of an implant as described herein.

In some variations, the ion-releasing implants described herein are configured as bone screws for treating a bone in need of treatment, such as a broken or osteoporotic bone. The ions released may be silver, zinc, or silver and zinc. Methods for treating a tissue (including bone) are also described herein. For example, an implant may be configured as a bone screw may align, biopsy, fuse, and/or stabilize a bone. The screw may eliminate, prevent, or reduce an infection, such as a bacterial, protozoan, or fungal infection. The treatment from the screw may provide support to the bone and may generate therapeutic silver ions to eliminate, prevent or reduce an infection.

In general, when two metals with different redox potentials are in electrical contact and immersed in an electrolyte, one metal may preferentially ionize and free electrons. As the free electrons migrate to the second metal, an electrical potential, called a galvanic potential, is created. The process requires an electron acceptor, such as oxygen near the second metal. When the first metal is silver, ionic silver is released. Similarly, if the first metal is zinc, ionic zinc is released.

The devices and systems described herein are controllable ion-releasing systems that are configured to allow the controllable release of ions (and particularly silver and/or zinc ions) into a body with sufficient concentration and distribution to prevent or treat infection in the tissue while also providing structural support to the region and preventing migration of the device. Various embodiments of these devices are described and illustrated, however the general theory of operation of all of these devices may be similar. The devices or systems may be configured as bone implants that treat bone and surrounding tissue, by release of ions such as silver ions.

FIGS. 1A-F describe a simple galvanic cell setup such as for use in a body. The setup is shown treating an infection, but the same process could be applied to healthy tissue to prevent an infection (prophylactically). The components including a first metal 2 (e.g., silver), second metal 4 (e.g., platinum), and electrolytic fluid 6 (e.g., blood) are shown individually in FIGS. 1A-1C and arranged in a tissue in FIGS. 1D-1F. Electrolytic body fluid 6 is shown bathing or contacting healthy tissue 10 as well as infected tissue 8. When silver metal 2 contacts platinum metal 4 in body fluid 6, it forms a galvanic cell with a silver anode and platinum cathode. As shown in FIG. 1E, ionic silver 12 is generated and spreads through the body fluid, killing microorganisms and creating an infection-free zone 14 in body fluid 16 in the vicinity of the anode. After treatment is complete, silver anode 2 may be removed 20 leaving an infection-free body fluid 18. Alternatively, platinum cathode 4 may be removed; alternatively both anode 2 and cathode 4 may be removed. Although the system is described using a silver metal anode and a platinum metal cathode, any metal with a higher redox potential than silver may be used as the cathode. The metal may be a noble metal, such as gold, palladium or platinum. For purposes of illustration, the silver anode will be described as the removable trigger for creating and stopping the galvanic response. However, either the silver or the metal with the higher redox potential can serve as a removable trigger (cartridge).

One embodiment of a device for controllably releasing silver is a bone stabilization device such, such as a bone screw. A bone stabilization device may include a support region (e.g., an elongate rod, tube, channel, or the like) for insertion into the bone, and an insertion engagement region (e.g., a head, shoulder, coupling, etc.) for engaging with an insertion and or removal tool. The insertion engagement region may be located at or near the proximal end, and may include an opening or engagement region for insertion and/or activation of a silver-release (e.g., galvanic silver release) cartridge. In some variations the engagement region includes a deployment mechanism (or contains an deployment mechanism) for activating and/or deploying silver-releasing members of a silver-releasing cartridge. The deployment mechanism may be referred to as a deployment trigger. Examples of this are provided below.

For example, a stabilization device for controllable release of silver may be configured as a silver-releasing bone screw. In general a silver-releasing bone screw is configured to controllably and/or activatably release silver to prevent and/or treat infection. A bone screw may include an elongate body (which may be threaded or otherwise include one or more bone engagement surfaces) and an engagement region at the proximal end configured as a head; one or more cartridges for galvanic release may also be included to allow the device to galvanically release silver. For example, a bone screw according to the disclosure may have a screw rod (elongate body) and one or more cartridges. The cartridge(s) may be configured to insert into the screw rod, and may be configured as an anti-infective cartridge or a biopsy cartridge or both. A bone screw may have a platinum metal cathode and a silver metal anode. In some variations the cathode and/or the anode (or just one or the other) may be present on the body of the bone screw; in other variations the cathode and/or anode (or both) may be present on a cartridge that can be inserted and/or removed from the bone screw. In some variations, the screw rod may be a platinum metal cathode and the anti-infective cartridge may be a silver metal anode. The cartridges may also include one or more anchoring, engagement, and/or stabilization members that are configured to extend from the bone screw and into the bone. These members may be configured as arms, fingers, spikes, ribs, probes, struts, or the like, and may extend from the body of the bone screw and into the tissue (including into the bone).

For example, in some variations, the screw rod is an elongated, cannulated (hollow), threaded rod. The rod may be externally threaded and/or internally threaded. Internal threads (or other guides/engagement regions) may be used to position and/or secure a cartridge within the body. The screw rod may be sized and elongated to fit a specific type of bone. The screw can fit any type of bone. By way of example, the screw can be configured to fit a femur, metatarsal, tarsal, tibia, or vertebra. Threads on the outer surface of the screw rod may anchor the screw rod into a bone or other body part. Thus, as mentioned, it may be threaded or may include other externally-facing engagement regions. The screw rod may be cannulated along its entire length, or along part of its length. The cannulated portion may create a fluid flow path. Fluid, such as oxygen carrying blood, may flow along the flow path and provide oxygen to create galvanic silver ion generation by the screw. In one example, the screw rod may be cannulated from a proximal end to part but not all of the way to a distal end. The screw rod may be solid along part of its distal end. The solid distal end may be used to deflect a portion (e.g., anchoring, engagement, and/or stabilization members) of a cartridge to be deflected from the cannulated inside to outside the screw rod, and may also provide additional stability and/or strength to the elongate body.

FIG. 2A shows one variation of a bone stabilization implant for delivering an antibiotic (e.g., silver) in a controllable manner to a region of bone and/or surrounding tissue. In this example the bone stabilization device is configured as a bone anchor screw including an elongated, cannulated screw rod 22 region. Screw rod 22 has elongated body 26 and threads 24. Threads 24 are configured to penetrate a part of a bone and/or to hold the screw in place in a bone or body region.

The screw may have a screw head 28 at a proximal end with one or more features to aid in holding, placing and/or removing the screw rod and for inserting and/or activating the cartridge. FIG. 2A shows one example of a screw head configured as a grippable screw head 28. The screw head may engage an insertion device and/or removal device. In some variations the screw may have a shaped head, such as hexagonal head 56 shown in FIGS. 5 and 6 that can be gripped by a wrench or other gripping tool. The feature may also be used to hold the rod screw in place while inserting or removing a cartridge or performing other manipulations.

The inside of the screw rod may have connection means for connecting with or attaching an insertion tool. In one example, the screw rod may have threads inside the screw rod (internal threads). The internal threads may be along part or maybe along the entire internal length of the screw rod.

The bone screw example shown in FIG. 2A includes a screw rod with a channel or opening 30. The screw rod may have just one channel or opening or may have more than one channel or opening. The channels or openings may be sized and shaped to allow at least part of a biopsy cartridge and/or anti-infective cartridge to move outside cannulated screw rod.

The shape and pitch of the screw rod external threads may be angled or shaped to aid or direct cartridge placement. FIG. 2A shows screw rod external threads 24 that may aid placement of a cartridge. The cannulated screw rod may have a port or ports (e.g., an opening) around the channel that is configured to guide a portion of a biopsy element and/or anti-migration/anti-infection element of a cartridge from inside the cannulated screw rod to outside.

The screw rod may be made of any biocompatible material that is sufficiently strong to be inserted into a body (bone) region. For example, the screw may be made, at least in part, of a steel (e.g., stainless steel), or other material. In some variations, the screw rod is made of platinum, titanium, or stainless steel material that is coated with platinum, palladium or gold. In particular, the screw rod may be coated with a material or materials that are able to create a galvanic response with silver. The coating may be over the entire surface of the screw rod or may be over part of the surface. The coating may be in the form of bands. The coating material may be a noble metal that has a greater galvanic potential than silver in a body. The noble metal may be gold, palladium, or platinum.

The rod screw may have features to increase its surface area. In particular, in variations in which the anode or, more likely, the cathode is located on the surface of the screw body, the portion of the screw body forming the cathode may have a relatively large surface area (particularly as compared to the opposite redox partner, e.g., anode). A larger surface area may create a higher galvanic current for generating therapeutic silver ions. The rod screw may comprise foamed metal on its inside surface, outside surface, or both surfaces.

Figure 5:
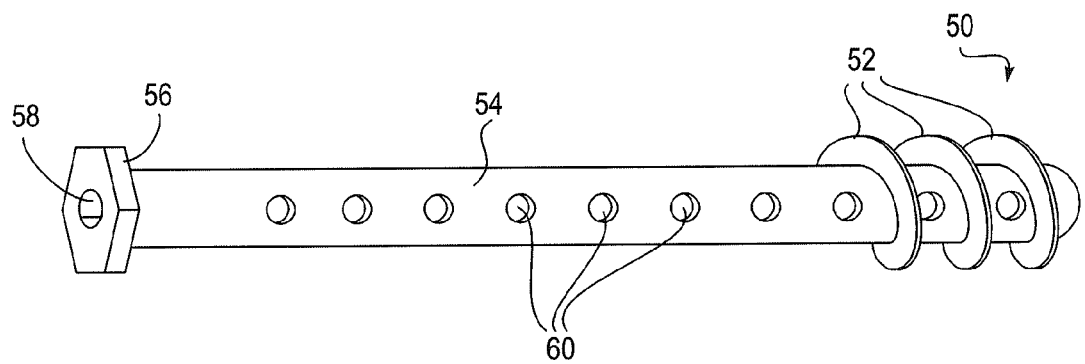
FIG. 5 is another variation of an implant.
Figure 6:
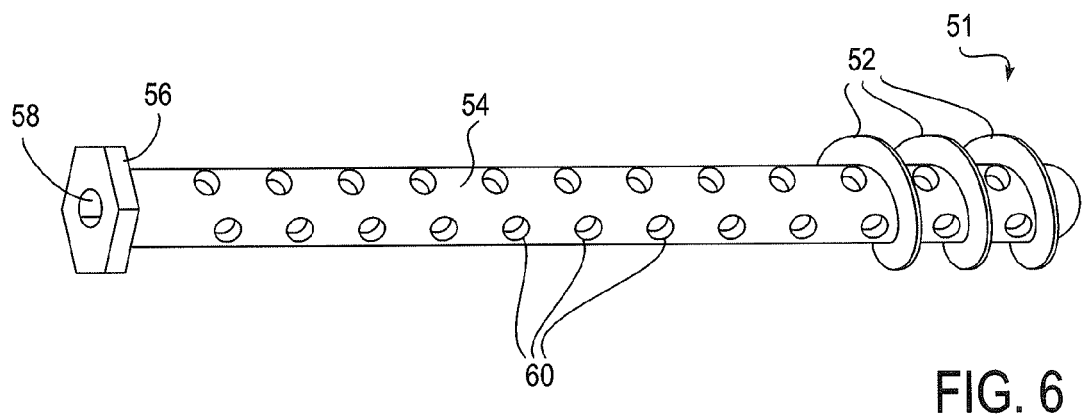
FIG. 6 is another variation of an implant.

In some variations the screw or rod configured as a stabilization device with controllable silver release may include on ore more features to increase opportunities for contact with body fluid. Increased contact may allow a stronger, faster, or longer galvanic response. FIGS. 5 and 6 show examples of rod screws 50, 51 with openings 60 along body 54 in addition to openings near threads 51. These openings may allow increased fluid flow, such as blood flow, around and through the rod screw. Some or all of these opening may also be configured to allow exit of one or more members (e.g., arms, struts, etc.) from a cartridge.

Any of the devices described herein may include or be configured for use with one or more cartridges. In general, a cartridge is a removable/replaceable element that may be inserted into or alongside of these support and antimicrobial devices (e.g., screws). As mentioned above, the cartridge may include one or more members that are configured to be extended out of the device and into the surrounding tissue. These members may be referred to and configured as struts, probes, legs, arms, hooks, wires, coils, fingers, spikes, ribs, or the like; in general they are elongate members that may be inserted into the patient's tissue and extend away from the body of the device. The members may therefore be configured to help secure the device within the tissue. For example, the members may enhance the mechanical attributes of the device, including preventing the device from pulling out of the tissue.

A cartridge may be referred to as an anti-infection cartridge if it is configured to aid in the release of silver ions from the device. For example the cartridge may include one or more members having silver (e.g., anode) regions or configured so that an entire member is silver releasing. In some variations the cartridge may also be referred to as a biopsy cartridge that is configured to remove tissue (e.g., bone, soft tissue, etc.) for testing. In some variations the cartridge may be configured as both an anti-infection and a biopsy cartridge.

An anti-infection cartridge may include a cathode. For example, the cartridge may include a plurality of arms, some of which are formed of a metal such as platinum that can react with the silver anode to release silver. As mentioned, in some variations the body of the implant device may include all or portion of the cathode.

In the examples illustrated herein the treatment cartridges are shown as separate elements that may be inserted into the devices. For example, a cartridge may be inserted into the device after the device (e.g., screw body) has been implanted into the bone. Cartridges may be replaced or recharged (e.g., replacing a portion of a cartridge such as a silver-containing member) without removing the entire device from the patient.

In some variations the cartridge is integral with (or part of) the implant device (e.g., screw).

The anti-infection cartridge may serve other functions in addition to or instead of being anti-infective. For example, it may be configured to prevent device migration. In some variations, including those illustrated below, a plurality of member extend from the device body (e.g., the body of the bone screw) and push into the tissue to help anchor the device. Thus, the cartridge member(s) may be configured to penetrate tissue, including bone. In some variations the members are rigid/stiff member and may also include tissue-penetrating distal regions. For example, one or more members may be stainless steel, nickel titanium, or the like (which may be coated with silver in some variations).

Thus, an anti-infection cartridge may comprise silver or a silver coating, plating, or the like. The anti-infective cartridge may be configured to be easily inserted and/or easily removed from the cannulated device (e.g., screw). In some variations, the cartridge has a holding end and a probe end. The holding end may be configured to be readily held, gripped or grabbed by a hand or by a device. By way of example, the holding end may be a loop, V shape or U shape, or may include a grip region. The probe end may be configured to contact a body part or a body solution. In general, the probe end is configured as one or more members that extend from the implant device when it is implanted. For example, the probe end may be configured as one or more members that extend from the screw rod. This may allow the silver ions to be directed to a particular body region, or it may create a larger region of therapeutic silver ions, or it may allow the cartridge to better contact or grip or hold a body surface.

Figure 2B:
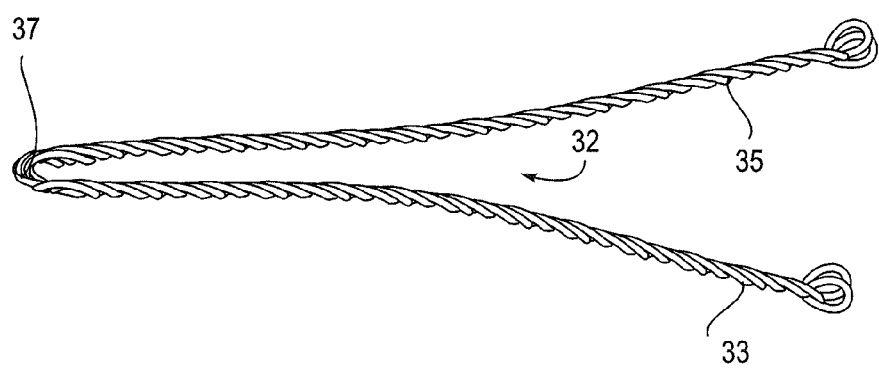

FIG. 2B shows one example of an anti-infection cartridge 32; the proximal end may be referred to as the holding end 37, which can be gripped by a hand or tool. The distal end of the cartridge in this example has two probe ends that can extend out of the body of the screw device. In FIG. 2B, the ends 33, 35 of the two members of the cartridge 32 can be inserted into a screw rod portion of a screw of rod for implantation into the body (bone). In this example the body of the screw rod includes a cathode 22 along the outer surface of the screw; the anodes on the elongate members of the cartridge contact the cathodal surface of the screw when they are extended from the implant. Each probe of the cartridge may have multiple probe ends. The probe ends may be configured to contact a portion of the bone or other tissue to hold the cartridge and bone screw in place. The probe ends may be positioned (spread apart) to create a larger area of effective silver ion area.

Figure 3:
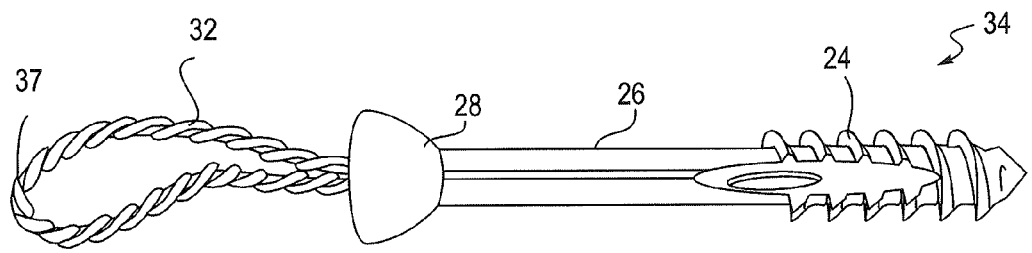
FIG. 3 shows another variation of an implant as described herein.
Figure 4:
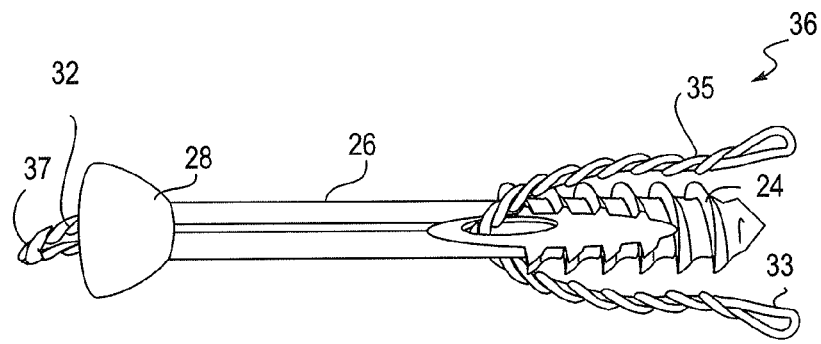
FIG. 4 shows the implant of FIG. 3 in a deployed configuration.

The anti-infective cartridge may be placed in contact with a screw rod to generate a galvanic screw in variations having the anode(s) on the cartridge and the cathode on the body of the implant (e.g., screw). For example, FIGS. 3 and 4 illustrate placement of an anti-infective cartridge 32 such as the one shown in 2B in contact with a screw body such as the one shown in FIG. 2A. The cartridge arms are extended in FIG. 4. In this example the cartridge includes two members, each formed of the twisted wires shown. In one variation the wires are both silver wires; alternatively one wire may be silver and the other wise stainless steel or the like, adding column strength for insertion, such as may be helpful for use in bone. For example, in FIG. 3 the probe ends of the cartridge pass through the center of cannulated screw rod 26 and may be held there until they are deployed into the tissue. When they are deployed (e.g., after implanting the device into the bone) the implant may include deflection/guide regions that steer the members out of the implant and into the tissue. For example, the threads 24 of the screw body in FIGS. 3 and 4 may receive or guide the probe ends as they exit. As the cartridge 32 is advanced, probe ends 33 and 35 exit through openings 30 in the screw body. As mentioned, extending the probes into the tissue may provide mechanical resistance to inhibit unwanted removal or movement of the probe and/or screw. In some variations the distal end of the probes may be sharp or otherwise tissue penetrating.

A biopsy cartridge may share many similarities with an antimicrobial cartridge as described above. For example, the biopsy cartridge may include one or a plurality of members configured to extend from the body of the implant device (e.g., arms, struts, etc.). In some variations the distal ends of these members may include one or more tissue capture elements such as a cup, hook, scraper, basket, needle, etc. A cartridge (including a biopsy cartridge) may also include an attachment site or coupling for a proximal handle (e.g., a threaded region or the like). In some variations a biopsy cartridge may be paired with an antimicrobial cartridge and the two may be exchanged from the same implant device. For example, the implant device (e.g., screw body) may be inserted and an antimicrobial cartridge and a biopsy cartridge may be alternately inserted to sample, then treat, then sample (in any appropriate order) the bone. In some variations the members of the biopsy device are longer (or are capable of extending to a longer length) than the members of the antimicrobial cartridge, to sample bone regions beyond the sites in which the members of the antimicrobial cartridge resided. In some variations the insertion length of the cartridge member(s) is variable, and may be selected or modified by a user when inserting or deploying the cartridge.

FIGS. 7A-C, 8A, 8B, 9A, and 9B describe another embodiment of a galvanic screw system for treating or preventing infection. These systems typically include a support device body (e.g., screw or rod body) and one or more cartridges, as described above. A screw system may have a collapsed or un-deployed configuration and an expanded or deployed configuration. In some variations, toggling between the deployed and un-deployed configurations controls the galvanic potential. For example, in some variations, extending the members of the cartridge including the silver anode may start the galvanic current by placing the anode in electrical contact with the cathode.

Additionally, because of the relatively streamlined initial size/shape, the un-deployed configuration of the system/device can readily be inserted into a bone in a less invasive way and expanded into the deployed configuration once it is place, limiting any damage or trauma to the tissue.

When the screw is in an un-deployed configuration, the galvanic potential is essentially off. When the screw is in an expanded position, the cathode and anode are in electrical contact with each other and the galvanic potential is on. As the amount of silver in the implant may be limiting, it may be useful to keep a galvanic potential turned off when it is not needed and conserve the potential for future use. The implant may be kept in the collapsed (off) or partially collapsed (off) configuration for any reason. For example, the implant may be configured to be switched "off" (stopping the galvanic release of silver) if there is no evidence of a current infection, but a future infection may be expected, as might be the case in a joint implant. Joint implants have been reported to develop infections months or years after being implanted. By implanting one of the devices as described herein for controllably delivering silver, but leaving galvanic potential "off", the implant may conserve the silver for use if and when an infection develops.

Thus the devices and systems described herein may be configured to allow the anode to be electrically isolated from the cathode (switching "off" the delivery of silver by the device) until it is desired to be controllably released. For example, the electrical connection between the anode and the cathode may depend upon the extent to which a cartridge having members is extended from the body of the device. In some variations, a conductive bridge (e.g., switch) between the anode and cathode may be moveable into and out of position to turn "on" or "off" the galvanic reaction. This is described below in reference to FIGS. 12A-12B. In other variations a switch is not necessary, as the anode and cathode may be place in electrical connection by fully or partially deploying the cartridge (e.g., the members of the cartridge); in the un-deployed configuration the anode may be electrically isolated from the cathode.

In some variations, the activation of the silver release from the implant may depend upon controlling exposure of the anode and/or cathode (which may be in electrical contact) to an electrolytic solution. For example, the cathode and/or anode may be retracted into the fluid-impermeable body of the device until it is desired to release silver ions.

Note that the controllable release of silver as described herein may also refer to the controllable distribution of silver released into the body. In some variations the pattern of distribution of the silver in the body may be determined in part by the arrangement of the member in the deployed configuration. As the members are expanded away from the body of the device (e.g., the screw body or rod body) a much larger pattern (e.g., "cloud") of silver ions having antimicrobial effects at a larger concentration could be achieved than in comparison to an implant or device having only a coating of silver, even actively released silver. In some variations, the implant may be configured to allow control of the extent of the deployment of the members; for example, extending the device only partially from the body of the device as illustrated in FIGS. 7A-8B.

Figure 7A:
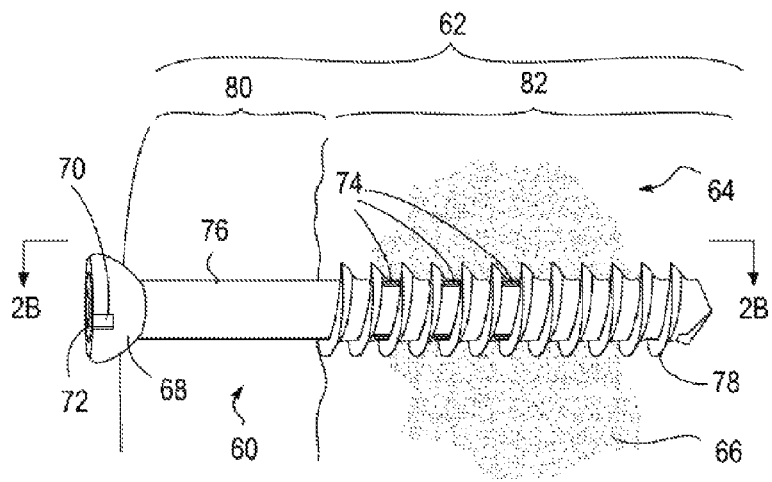
FIGS. 7A-7C illustrate deployment of a silver eluting bone implant as described herein.
Figure 7B:
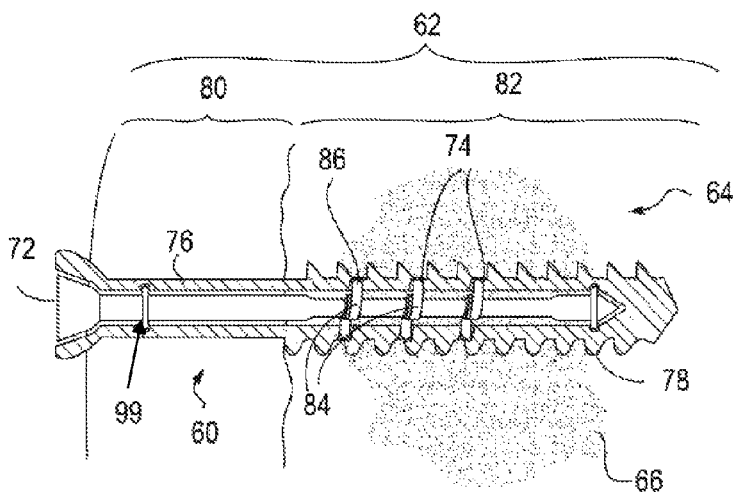
Figure 7C:
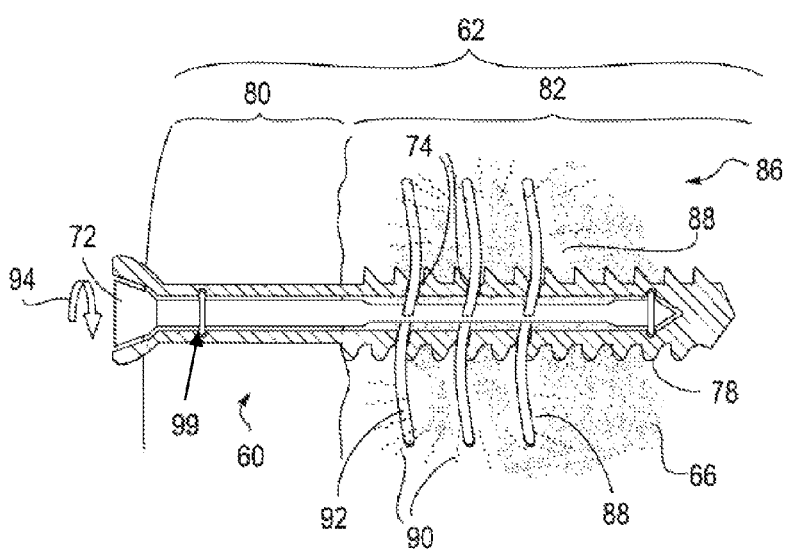

FIGS. 7A-7C show a device for controllably delivering silver ions that is configured as a screw 60; in this example, the screw has been inserted in a bone 62 having a infected region 66. The implant is bathed in a body fluid 64. FIGS. 7B-7C show views along line 2B of FIG. 7A, showing the internal cannulated passage through the elongate screw body 76. The implant is anchored in cancellous bone 82 initially by threaded portion 78, with the rest of implant body 76 in this example positioned within the cortical bone 80. In this example, six members formed as anodes (silver containing regions) are configured as ribbon coils 84 that can be rotated to deploy them out of openings 74 on the body of the screw. The ribbon coil 84 is held inside rod screw 60 near slots/openings 74 between threads 78. These deployable members are part of the loaded (e.g., preloaded) antimicrobial cartridge 72. The cartridge may be rotated when positioned within the screw body to deploy the members from the screw and into the tissue. The device also includes a screw head 68 at the proximal end and a deployment trigger 72 which is configured as a trigger head 72 in this example. Screw head 68 has slots 70 which can be used to insert (e.g., screw in) the screw into the bone, and/or to hold screw body when manipulating trigger head 72 or can be used to otherwise insert, remove, or manipulated the screw.

In the exemplary device shown in FIGS. 7A-7C, the silver releasing members of the cartridge may be deployed by rotating the trigger. Referring to FIG. 7C, the trigger head 72 may be rotated (e.g. counterclockwise), causing ribbon coils 84 to move into position under slots 84 and to unfurl to form probes 88 that extend from the elongate body of the screw. As the members extend from the body, silver on the members (forming a cathode) is placed in electrical contact with the cathode formed on the outer surface of the screw body 76; thus the galvanic potential is on, and silver may be released into the tissue that is bathed in the electrolyte solution (e.g., blood). Thus, members 88 include a silver-releasing anode that is electrically communicating with the platinum cathode on the screw body 76. In this manner, silver ions may be released in a region surrounding the implanted screw body, and silver ions 90 may clear infection 66 to create a clear zone 88 in tissue around the implant.

In the example shown in FIGS. 7A-7C the device for antimicrobial silver release may include a cartridge having the coiled arms that can be extended from the body. In some variations, the cartridge is integral with the body of the device. For example, in FIGS. 7A-7C the cartridge comprises the inner rod member connected proximally to the trigger; the cartridge includes the coiled member wrapped around the inner rod member. The inner rod member may be rotated within the body. In some variation the inner rod member is permanently fixed within the body of the device. In some variations the inner member forming the rotatable may be removable from the body of the device. Thus, the inner member may be recharged and/or replaced while leaving the screw within the patient's bone.

Figure 8A:
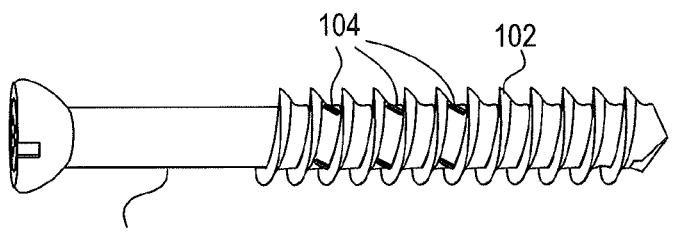
FIGS. 8A and 8B illustrate deployment of another silver eluting bone implant.
Figure 8B:
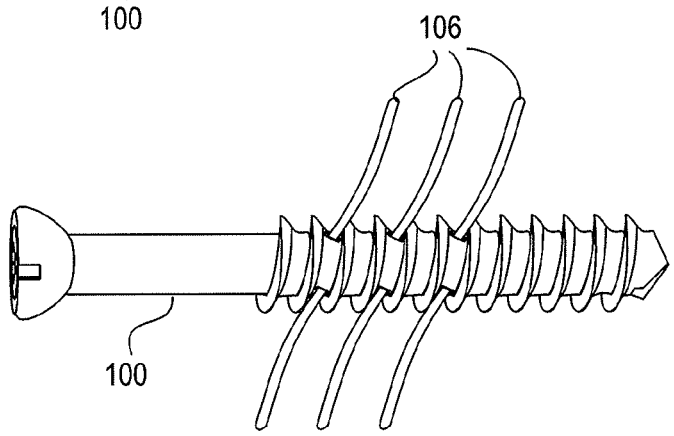

FIGS. 8A and 8B show another variation of a device configured as a screw similar to the one in FIG. 7 A-C with tilted slots 104 between threads 102 on rod region 100 in order to bias ribbon coil 106 to exit the body at an angle. In general, the device body may include one or more guides, channels, or the like for directing the members ("ribbon coil 106") from the cartridge (e.g., inner rod) away from the body of the device at an angle or along a pathway. For example, in some variations the device's threads near the distal end of the device may be used to deflect and direct the extending members and thereby control the extent and location of antimicrobial "cloud" surrounding the implant as the ions are released.

Figures 9A, 9B:
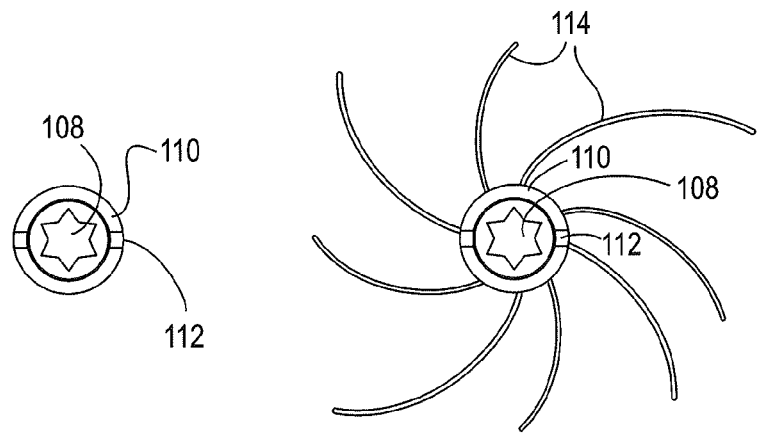
FIGS. 9A and 9B show a top view of an implant in a deployed an un-deployed configuration.

FIGS. 9A and 9B show a top view of another variation of a device configured as a screw similar to the ones shown in FIGS. 7A-8B. This variation includes more members (probes 114), which may be distributed more tightly or specifically around the device. In this example, the trigger head 108 is shown inside rod screw head 110. Slots 112 on screw head 110 can be used to hold the device head 110 relative to trigger head 108 to manipulate the trigger relative to the screw, or screw relative to the bone. In another example, the interior surface and/or outer surface of the screw head 110 may be shaped to engage and/or be grippable by a cannula or other insertion/removal device during screw insertion, removal, or repositioning. The internal shape of the proximal end of the device may be any shape that allows an insertion/removal device to grip the internal surface and to move (e.g. rotate) the screw. The internal shape may be, for example, hexagonal, square, triangular, or threaded. The internal shaping may be only in the head or may extend through part or the entire length of the screw. Being able to grip more than just the head of the screw may better distribute force applied (e.g. torque) to move the screw (e.g., during insertion, removal or repositioning) and thereby prevent the screw from breaking, stripping, or otherwise being damaged. When the multiple arms (probes, coils, etc.) are extended into the tissue (e.g., bone) from within the bone implant device, these member may (in addition to releasing silver) provided additional anchoring to the implanted device. For example, the extended/deployed arms provide mechanical resistance to inhibit unwanted removal or movement of the device.

Figure 10A:
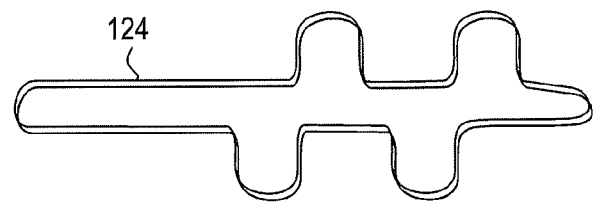
FIGS. 10A-10D illustrate variations of silver eluting bone implants as described herein.
Figure 10B:
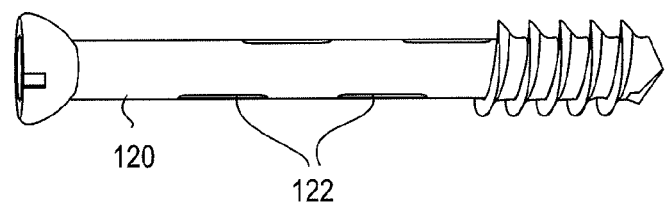
Figure 10C:
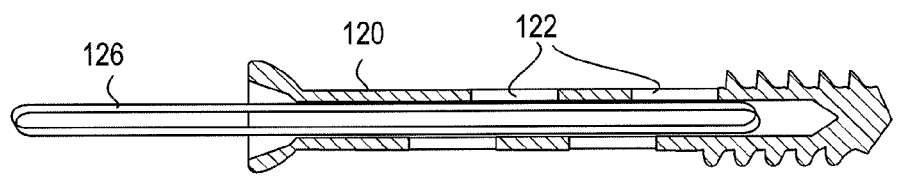
Figure 10D:
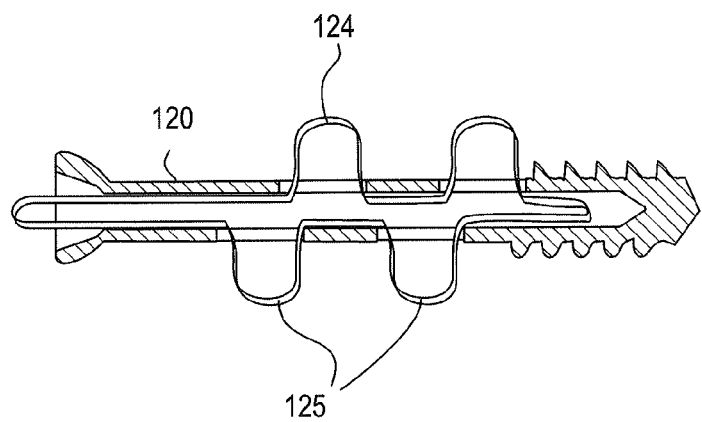

In general, the cartridges described herein can be assembled from any materials that will allow them to be deployed from an implanted device and release silver ions and/or remove (biopsy) tissue. For example, FIGS. 10A-10D show a device, configured as a screw, and a cartridge, formed from a memory shaped ribbon. FIG. 10A shows the shape of the ribbon 124 and the screw device 120. In this example, ribbon 124 collapses to assume collapsed configuration 126 as it's inserted into housing 120. Collapsed ribbon 126 is pushed or turned into position so that probes 125 can expand through slots 122.

Figure 11A:
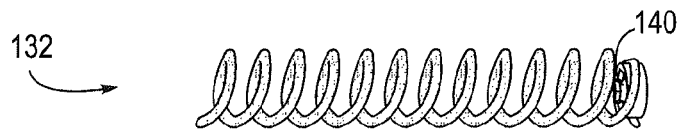
FIGS. 11A-11C illustrate another variation of an implant.
Figure 11B:
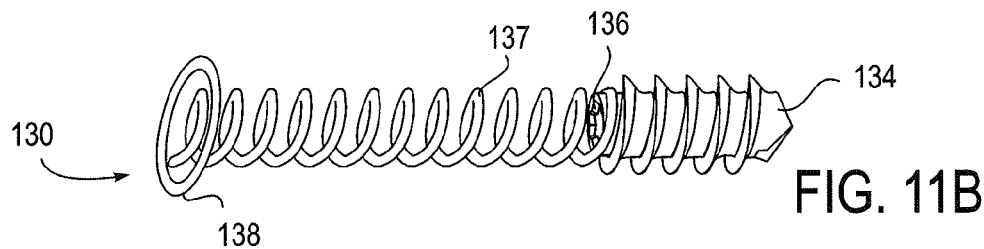
Figure 11C:
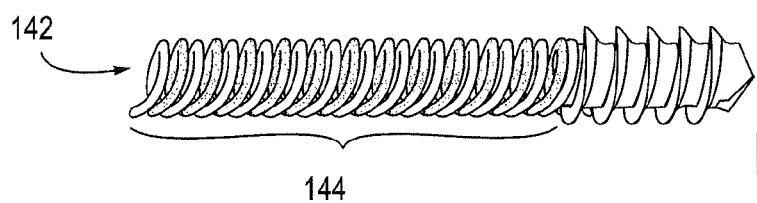

Bones that have been subject to mechanical trauma, infection or other forms of insult may be prone to further damage during insertion of a bone screw. Inserting a bone screw with mechanical properties that are closer to those of bone may reduce or prevent further trauma. FIGS. 11A-C show a bone screw in which the mechanical properties of the bone screw are relatively similar to the mechanical properties of the bone, but which is still able to generate therapeutic silver ions. In this example the elongate body of the device 130 includes a threaded distal end region and a proximal spring region. The device is shown in FIG. 11B and the cartridge for use with the device is shown in FIG. 11A. FIG. 11B shows a platinum (or platinum coated) screw with a threaded distal end 134 and a proximal spring end 137. Screw end 134 may be inserted into a bone by turning hex 136 with a driver. In any of the variations described herein, an initial (e.g. pilot) passage into the bone may be drilled or otherwise formed before implanting the device. Stop 138 may be used to prevent the screw from being inserted too far into the bone. Once rod screw 130 is in place, a cartridge comprising, in this example, a silver screw or spring 132 as shown in FIG. 11A can be screwed into rod screw 130. The result is the two springs coiled together 144 as shown in FIG. 11C. The contact between the platinum or platinum coated coiled region of the device body 137 and the coiled and silver or silver coated region of the cartridge 132 is sufficient that when in the presence of an electrolytic solution, silver ions will be released from the implant.

Figure 12A:
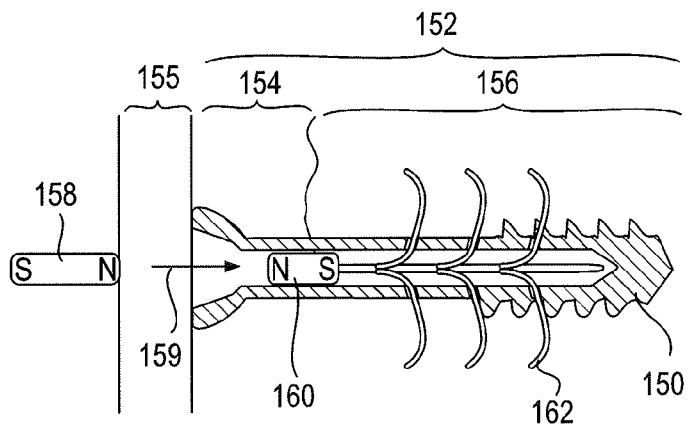
FIG. 12A shows another variation of a silver-eluting implant in a deployed and activated configuration (e.g., with silver release members extended into the tissue)
Figure 12B:
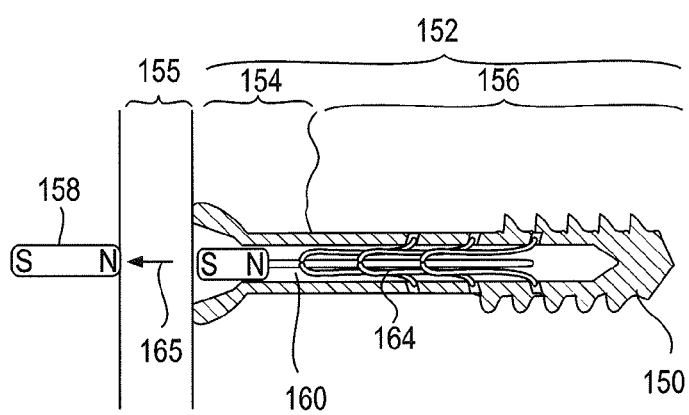
FIG. 12B shows the same implant in a de-activated configuration, in which the silver release members have been withdrawn into the lumen/channel of the implant.

Another example of a trigger or switch for controlling the release of silver ions (e.g. for creating a device having a controllable on/off application of silver ions) uses a magnet as shown in FIGS. 12A-12B. In this example a control magnet is shown outside the body, external to skin 155 while screw 152 is shown screwed into cortical 154 and cancellous 156 regions of bone 152 in the body. Application of external magnetic force (e.g., magnet 158) repels or attracts a corresponding magnetic region within the implant 160, causing it to move the cartridge 162 into or out of position to expand probes 162 out of screw 150 or retract them into the screw. For example, in FIG. 12B, application of external magnet 158 attracts the internal cartridge implanted with the screw, causing it to move the cartridge 164 towards it in a contracted position. Lateral movement of the cartridge results in extending or retracting the members of the cartridge into and out of the screw body, thereby turning on or off the release of silver ions from the screw.

In use, several bone screws can be used together for larger bones or bones otherwise requiring more support or treatment as shown in FIGS. 13A-13B. For example, FIG. 13A shows a series of bone screws 190 inserted through a bone plate 190 that is adjacent to a cortical bone 194 and treating large infection 188 near fracture 186 in femur 180. Each screw has multiple silver-releasing members 194 extending into cancellous bone 184 to create a large silver therapeutic area. FIG. 13B shows an alternative embodiment in which some silver/silver coated rod screws 196 are alternating with platinum plated or noble metal rod screws 198.

Figure 15:
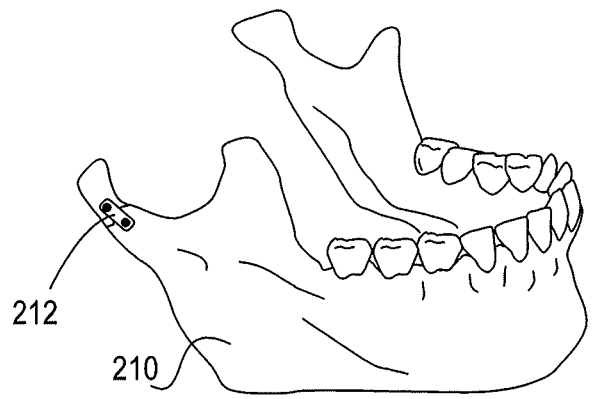
FIGS. 15 and 16 illustrate variations of silver eluting bone implants configured to treat other bone regions, including the jaw and skull (face), respectively.
Figure 16:
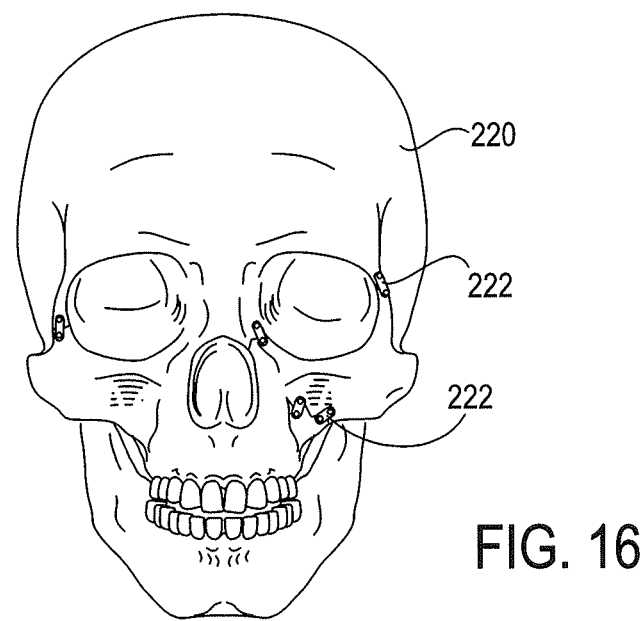

The bone screw, methods, and systems described herein may be used with any type of bone, including long bones. FIG. 14 shows a bone screw 202 configured to release silver ions similar to those in FIGS. 2A-3B above, inserted into a portion of a jaw. Therapeutic silver ions 206 are released from members 206. The screw may be configured to attach a tooth, crown or other dental appliance. FIG. 15 shows bone screws and a plate attached to a mandible such as might be used in a reconstructive surgery to prevent or treat infections. FIG. 16 shows bone screws and plates used in various bones of the jaw, face, and skull 220.

In some variations, the anti-infective cartridge includes a lock on the cannulated screw and/or rod to hold the cartridge in place relative to the elongate body of the device. Thus, the cartridge may be locked in a configuration (e.g., deployed, un-deployed, etc.) within the body of the device. The lock may be releasable; for example, the lock may include a latch.

As mentioned above, the cartridge may be configured as a biopsy (e.g., assay) cartridge, which may be used instead of, or in addition to an anti-infection cartridge; in some variations the cartridge is a combination of both anti-infective and biopsy. In general a biopsy cartridge may be coupled to the body of the device and used to withdraw a sample of tissue from around where the implant has been inserted without having to remove the device ("implant") from the body. For example, in some variations, the biopsy cartridge is inserted through the cannulated elongate body of the device (e.g., of a screw body) and one or more members of the cartridge extends from the elongate body, similar to the silver-releasing members extending from the silver-release cartridges described above, to make contact with a portion of the body to be assayed, to obtain a biopsy (assay) sample, and to be removed. The biopsy sample can be assayed in any way after being removed from the patient. Thus, the biopsy cartridge may have an expanded (deployed) form and a collapsed (un-deployed) form. The biopsy cartridge may be expanded before obtaining a biopsy sample and may be collapsed after obtaining a biopsy sample. Any of the structures described in the disclosure for the anti-infective cartridge and any of the methods described for inserting, using, or removing the cartridge may also or instead be used for the biopsy cartridge.

Although many of the examples described above are configured so that the device body is configured as the cathode (e.g., comprising a platinum material) while the extendable members from the cartridge are the anode material (e.g., silver or silver coated), in some variations this configuration may be reversed. For example, the device body (e.g., the screw body, rod body, etc.) may be silver or silver coated and the anti-infective cartridge may configured as the cathode, comprising a noble metal such as gold, palladium or platinum to create a galvanic response in the body and release silver ions.

In general, the devices may be inserted or implanted into the body, e.g., into the bone, either before during or after engaging a cartridge, including an anti-infective and/or biopsy cartridge. For example, a device configured as a silver-delivering screw may be inserted into a bone, loaded with an anti-infective cartridge or biopsy cartridge by inserting the cartridge through the elongate body (e.g., from the proximal end of the screw rod). A biopsy cartridge may be inserted and removed before, after, or instead of insertion of an anti-infective cartridge. In one example, a biopsy cartridge is inserted through the device body, takes a biopsy sample, and is removed before anti-infective cartridge is inserted. In another example, an anti-infective cartridge may be inserted, left in the body for a period of time to create therapeutic silver ions, and removed before a biopsy cartridge is used to remove a biopsy sample to determine an effectiveness of anti-infective treatment. In another example, an anti-infective cartridge may be inserted, left in the body for a period of time to create therapeutic silver ions, and removed before a biopsy cartridge is used to remove a biopsy sample to determine an effectiveness of anti-infective treatment.

In another example, a first anti-infective cartridge is placed through the device implanted in the body and one or more anti-infective cartridges are additionally placed in the device body, without removing the first anti-infective cartridge. The cartridges may degrade (e.g., corrode as the silver is release) or simply avoiding by preceding cartridges.

In another example, a first anti-infective cartridge may be removed from an implanted device in a body and a second anti-infective cartridge inserted. This process may be repeated. This may be done, for example, if there is insufficient therapeutic silver remaining on a first cartridge. The screw rod and any of the cartridges may be left in the body for any length of time. They may be left in for less than thirty days (e.g. a few days, a week, or several weeks) or they may be left in for more than thirty days. In one example, the screws may be left in permanently.

EXAMPLES

Any of the exemplary ion-releasing devices described above may be used to treat (or prophylactically treat or prevent) infection and/or support tissue. Exemplary methods of use are illustrated below. These examples are intended only to illustrate how one such implant may be operated, and is not intended to be limiting or limited to any specific variation.

In general, the implants for controllably providing antimicrobial treatment and support may be used to treat any tissues of the body, but particularly bones, including the long bones (such as the femur, tibia, radius, ulna, fibula, metacarpal, metatarsal, phalanges, etc.), the spine, and the skull. In some variations the device is configured for insertion into the medullary canal of a lower extremity bone, such as a femur, tibia, tarsal or metatarsal, for the alignment, stabilization, fixation and bone biopsy of various types of fractures or deformities caused by trauma, infection or disease. Examples of such fractures include: traumatic fractures, re-fractures, non-union, reconstruction, malunion, malalignment, pathological fractures due to infection or disease and impending pathological fractures. The ion controlled release systems may have silver and/or zinc coated struts that expand out from the body of the device to form a three-dimensional array to stabilize, minimize device migration and form an antimicrobial barrier to reduce microbial colonization on the external surfaces of the device.

An implant that controllably provides antimicrobial treatment, such as a bone screw for controllably releasing silver ions, may be used to repair a bone fracture. The bone may first be prepared to receive the device. Pre-existing deformities may be corrected prior to the preparation and insertion of a device such as those described above configured as a controllable silver-ion releasing bone screw (e.g., intramedullary or IM screw). The anatomy of the deformity, surgeon preference, and patient positioning may determine the appropriate approach chosen for joint preparation and alignment.

For example, a bone implant that controllably provides antimicrobial treatment may be use used to repair a broken ankle. Upon properly aligning and preparing all the joint surfaces, the ankle may be positioned for arthrodesis. The ankle may be medizlized by thorough debridement of medial gutter facilitates positioning in the center of the calcaneus, talus and tibia. The ankle may then be placed in neutral dorsiflexion and symmetric external rotation of the contralateral ankle. This position may be maintained throughout the procedure, and may be facilitated by provisionally placing a wire on the periphery of the ankle joint.

Under fluoroscopic control, a 2-3 cm longitudinal incision may be made just above the location for the bone insertion point. After the incision is made, dissection may be continued down to the surface of the target bone by bluntly dissecting through the soft tissues, noting the location of neurovascular bundles. Thereafter, the device (e.g., a controlled silver ion releasing implant or bone screw) may be inserted. An introducing cannula can then be selected and placed against the bone insertion point. The hand reamer may then be used to carefully ream through the cortical bone into the intramedullary canal. The cannula is not advanced into the bone. The position of the hand reamer under fluoroscopy may be monitored under floro periodically. The hand reamer can be removed from the cannula.

Thereafter, the surgeon may select the proper size implant device IM screw rod that is pre-mounted on trocar. Advance the screw rod into the bone by turning clockwise. Periodically stop and check under fluoroscopy the position of the screw rod with respect to the opposite cortical side.

Finally, the trocar device may be removed from the inside of the cannulated screw rod by turning clockwise.

In some variations, the bone implant that controllably provides antimicrobial treatment may also be used to take a biopsy before, during or after insertion of the implant. The implant may be inserted into the bone as discussed above, and a bone biopsy cartridge may be inserted through the internal cannula of the implanted device. The proximal end of the cartridge may be grasped direction of coupled to a handle for manipulation by a surgeon. The distal end of the biopsy cartridge may include one or a plurality of cupped wires that can be extended from the implant body and used to sample the tissue. For example, one or more cupped wires may be deployed through the ports of the body of a screw-type implant. This may be met with some resistance from the cancellous bone. Extension of the biopsy cup wires can be confirmed by fluoroscopy. After deployment of the wires, the proximal end of the cartridge may be pulled back and the wires retracted, capturing cancellous bone for biopsy in the cups of the cartridge. The cartridge may be removed from the rest of the implant, and placed in a sealed, labeled laboratory infectious disease container for further processing.

In general, the antimicrobial cartridges described herein may be inserted and/or deployed as mentioned above. For example, a cartridge may be removed from a foil sterile package. The cartridge may be stored in a sealed package with an indicator to indicate if the package integrity has been compromised. For example, the package may include an indicating desiccant (e.g., pouch) that visually indicated, e.g., by a line that changes red, if the packaging has been breached and exposed to humidity.

The cartridge may be inserted into the device housing, e.g., the central bore or cannula within the elongate cannulated body. In some variations the cartridge is pre-loaded into the body of the device. The cartridge, and particularly the elongate members of the cartridge at the distal end, may be inspected and/or aligned with the cannulated body so that they may be extended through openings in the body to extend from the body when implanted. The cannulated body may include a guide, channel, keying, etc. to aid in aligning and inserting the cartridge into the body. In some variations the inner surface of the cannulated body is keyed (including threaded) to guide the insertion of the cartridge; an outer surface of the cartridge may mate with and engage the inner surface of the cannulated body.

An insertion tool (e.g., handle) may be used to help insert the cartridge into the elongate cannulated body of the implant. For example, the insertion/removal tool may be an elongate rod having a coupling and or mount its distal end region to connect to a cartridge. In some variations the insertion/removal tool may include an inner body region for holding the cartridge in the collapsed/un-deployed configuration after or before it has been connected/removed from the implant body. For example, the cartridge may be "collapsed" by the action of the insertion tool. The distal end of the insertion tool may include a chamber, cannula, etc. for holding the cartridge in a collapsed configuration; the cartridge may be pushed out of or otherwise extended from the handle into the implant, allowing the members of the cartridge to extend through the body of the device and into the tissue.

Thus, the distal ends of the members may be extended away from the body of the implant and into the patient tissue so that the members will deploy through the ports of the device. In some variations this deployment is guided by the implant body which deflects and/or guides the members as they are extended. For example, the threads of an implant configured as a bone screw may be arranged to deflect the members outward and into the tissue. After insertion and/or deployment of the cartridge in variations requiring it, any inserter tools may be withdrawn and proper positioning may be confirmed using fluoroscopy.

Thereafter, the stability and operation of the device may be verified, and the surgical access/insertion site may be closed, at least for some amount of time. In some variations the cartridge may be replaced/recharged into the same implant over the course of weeks, months or years.

Once the implant has exceeded its useful life, it may be removed from the patient or left in place. In some variations it may be desirable to leave the implant in place so that it can continue to provide structural support. This may be true even of the cartridges, as any extended members that have been extended into the tissue may continue to provide structural support even if the source of silver ions has been exhausted.

The cartridges may be removed in many cases by reversing the insertion process just described. In some variations the cartridge may remain within the bone for approximately 30 days or more. The implant may be removed with a removal device configured to couple to the proximal end of the cartridge and/or to release the cartridge from the device body.

In some variations a retrieval kit may be used. For example, a retrieval kit may include a removal device (configured similarly to an inserter). To remove the device, surgical aseptic technique (under fluoroscopy) may be used to make a small incision directly above the site of the previous surgery. The removal device (cartridge retrieval device) may be inserted and attached to the proximal end to the outer housing to stabilize it. In some variations the retrieval device has an elongated body with a distal end that is adapted to couple or abut the implant device body and a second region that is configured to couple with the proximal end of the cartridge. For example, the retrieval member may include a central shaft having a distal end adapted to couple (e.g., screw onto) the proximal end of the cartridge and an outer cannula surrounding the central shaft that is configured to couple to the proximal end of the implant device. In some variations the retrieval device includes a proximal forceps that may be used to couple to the inner cartridge. Such configurations (or similar configurations) may allow sufficient leverage to remove the extended members and withdraw the cartridge form the implant and the body, retracting the members through the outer housing ports and collapsing them for removal.

After removal, the cartridge may be disposed of or used to provide biopsy material. The surgical site may be examined directly and by fluoroscopy. If it appears that the site (and implant) would benefit from additional anti-migration or anti-infection elements, a new cartridge may be re-deployed for another treatment period (e.g., 30 days) and the process repeated.

Although the illustrations described above illustrated primarily threaded screw variations, it should be apparent that non-treaded variations and non-screw variations are contemplated. For example, the devices for controllable release of silver ions described herein may be configured as nails, rods or the like.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What may be claimed is:

1. An implant for providing antimicrobial treatment to a bone, tissue or organ, the implant comprising:
   an elongate body having a threaded outer screw region;
   an inner channel within the elongate body;

a plurality of exit channels extending from the inner channel and out through the elongate body; and a treatment cartridge configured to mate with the inner channel and comprising a plurality release members, each release member configured to extend from the cartridge body out through an exit channel and to galvanically release silver, zinc, or silver and zinc, wherein the treatment cartridge is configured to retract the release members into the cartridge body.

2. The implant of claim 1, wherein the treatment cartridge has a helical region.

3. The implant of claim 1, wherein the treatment cartridge degrades as the silver, zinc, or silver and zinc is released.

4. The implant of claim 1, wherein the treatment cartridge comprises a guide to aid in aligning the treatment cartridge within the elongate body.

5. The implant of claim 1, wherein the treatment cartridge is configured to engage with an insertion tool for insertion into the inner channel.

6. The implant of claim 1, wherein the elongate body comprises a coating of silver, zinc or silver and zinc adapted to be galvanically released.

7. The implant of claim 1, wherein the release members comprise a coating of silver, zinc or silver and zinc adapted to be galvanically released.

8. An implant for providing antimicrobial treatment to a bone, tissue or organ, the implant comprising:

an elongate body having a threaded outer screw region and a sharp distal end;

a first coating forming a band around the threaded outer screw region of one or more of platinum, palladium and gold; and a second coating of one or more of silver, zinc, or silver and zinc, wherein the second coating contacts the first coating and is configured to corrode when the implant is inserted into the bone, tissue or organ and galvanically release one or more of silver, zinc or silver and zinc as the second coating is corroded in the presence of an electrolytic solution;

a treatment cartridge configured to engage an inner chamber within the elongate body, wherein the second coating is on the treatment cartridge, wherein the treatment cartridge comprises a guide to aid in aligning the treatment cartridge within the elongate body.

9. The implant of claim 8, wherein the treatment cartridge degrades as the silver, zinc, or silver and zinc is released.

10. The implant of claim 8, wherein the treatment cartridge is configured to extend release members out of the cartridge body.

11. The implant of claim 8, wherein the treatment cartridge is configured to engage with an insertion tool for insertion into the inner channel.

12. An implant for providing antimicrobial treatment to a bone, tissue or organ, the implant comprising:

an elongate body having a threaded outer screw region;

an inner channel within the elongate body;

a plurality of exit channels extending from the inner channel and out through the elongate body; and a treatment cartridge configured to mate with the inner channel and comprising a plurality release members, each release member configured to extend from the cartridge body out through an exit channel and to galvanically release silver, zinc, or silver and zinc, wherein the treatment cartridge comprises a guide to aid in aligning the treatment cartridge within the elongate body.

13. The implant of claim 12, wherein the treatment cartridge has a helical region.

14. The implant of claim 12, wherein the treatment cartridge degrades as the silver, zinc, or silver and zinc is released.

15. The implant of claim 12, wherein the treatment cartridge comprises a guide to aid in aligning the treatment cartridge within the elongate body.

16. The implant of claim 12, wherein the treatment cartridge is configured to engage with an insertion tool for insertion into the inner channel.

17. The implant of claim 12, wherein the elongate body comprises a coating of silver, zinc or silver and zinc adapted to be galvanically released.

18. The implant of claim 12, wherein the release members comprise a coating of silver, zinc or silver and zinc adapted to be galvanically released.

* * * * *